United States Patent
Tregger et al.

(10) Patent No.: US 12,106,237 B2
(45) Date of Patent: Oct. 1, 2024

(54) CONCRETE PLACEMENT SENSING USING AERIAL DRONES

(71) Applicant: GCP Applied Technologies Inc., Alpharetta, GA (US)

(72) Inventors: Nathan A. Tregger, Northborough, MA (US); Mark F. Roberts, North Andover, MA (US); Jason Straka, Danville, CA (US); Elise Berodier, Lausanne (CH); Greg Austin, Acton, MA (US); Robert Hoopes, Andover, MA (US)

(73) Assignee: GCP APPLIED TECHNOLOGIES INC., Cambridge, MA (US)

( * ) Notice: Subject to any disclaimer, the term of this patent is extended or adjusted under 35 U.S.C. 154(b) by 0 days.

(21) Appl. No.: 17/681,836

(22) Filed: Feb. 27, 2022

(65) Prior Publication Data

US 2022/0180270 A1    Jun. 9, 2022

Related U.S. Application Data

(62) Division of application No. 16/941,494, filed on Jul. 28, 2020, now Pat. No. 11,295,248.
(Continued)

(51) Int. Cl.
G06Q 10/06    (2023.01)
G06Q 10/0631    (2023.01)

(52) U.S. Cl.
CPC .  *G06Q 10/06311* (2013.01); *G06Q 10/06313* (2013.01)

(58) Field of Classification Search
CPC .................................................... G06Q 10/06
See application file for complete search history.

(56) References Cited

U.S. PATENT DOCUMENTS

| 3,053,673 A | 9/1962 | Walker |
| 3,100,526 A | 8/1963 | Martin |

(Continued)

FOREIGN PATENT DOCUMENTS

| CA | 2784424 C | * | 4/2014 | ............. C04B 14/06 |
| CA | 2962684 A1 | * | 9/2017 | ......... B28B 23/0031 |

(Continued)

OTHER PUBLICATIONS

Gene F. Sirca Jr., Hojjat Adeli, Infrared Thermography for Detecting Defects in Concrete Structures, Department of Civil, Environmental, and Geodetic Engineering, The Ohio State University, Journal of Civil Engineering and Management, vol. 24 Issue 7, 2018. (Year: 2018).*

(Continued)

*Primary Examiner* — Kurtis Gills
(74) *Attorney, Agent, or Firm* — NIELDS, LEMACK & FRAME, LLC

(57) ABSTRACT

Described are a method and system for coordinating the delivery and placement of concrete loads at a job site, and more particularly to adjusting a set time value or value range of the concrete loads, thereby to facilitate finishing or other concrete placement activities. In exemplary embodiments, the adjustments can be made based on an assessment of previously placed concrete loads. The set time values or value ranges of the concrete can be monitored and adjusted to achieve desired properties during installation and/or in its hardened state.

12 Claims, 10 Drawing Sheets

Related U.S. Application Data

(60) Provisional application No. 62/881,614, filed on Aug. 1, 2019.

(56) References Cited

U.S. PATENT DOCUMENTS

| | | |
|---|---|---|
| 3,234,154 A | 2/1966 | Martin |
| 3,662,830 A | 5/1972 | Martin |
| 3,885,985 A | 5/1975 | Serafin et al. |
| 4,089,895 A | 5/1978 | Jager |
| 4,182,191 A * | 1/1980 | Ikeda .................. G01N 33/383 |
| | | 73/803 |
| 4,190,454 A | 2/1980 | Yamagisi |
| 4,210,455 A | 7/1980 | Metcalf et al. |
| 4,466,836 A | 8/1984 | Crump |
| 4,676,832 A | 6/1987 | Childs |
| 4,943,930 A | 7/1990 | Radjy |
| 4,964,917 A | 10/1990 | Bobrowski et al. |
| 5,215,585 A | 6/1993 | Luthra et al. |
| 5,221,386 A * | 6/1993 | Ensminger ................ E04C 2/06 |
| | | 156/348 |
| 5,268,111 A | 12/1993 | Metz et al. |
| 5,417,759 A | 5/1995 | Huddleston |
| 5,427,617 A | 6/1995 | Bobrowski et al. |
| 5,634,972 A | 6/1997 | Pacanovsky |
| 5,952,561 A | 9/1999 | Jaselskis |
| 6,042,258 A | 3/2000 | Hines et al. |
| 6,042,259 A | 3/2000 | Hines et al. |
| 7,246,009 B2 | 7/2007 | Hamblen et al. |
| 7,265,846 B2 | 9/2007 | Forsyth |
| 7,968,178 B1 | 6/2011 | Scurto et al. |
| 8,020,431 B2 | 9/2011 | Cooley et al. |
| 8,118,473 B2 | 2/2012 | Compton et al. |
| 8,311,678 B2 | 11/2012 | Koehler et al. |
| 8,491,717 B2 | 7/2013 | Koehler et al. |
| 8,599,646 B2 | 12/2013 | Parrot |
| 8,727,604 B2 | 5/2014 | Compton et al. |
| 8,764,273 B2 | 7/2014 | Koehler |
| 8,818,561 B2 | 8/2014 | Koehler et al. |
| 8,858,061 B2 | 10/2014 | Berman |
| 8,874,283 B1 | 10/2014 | Cavote |
| 8,913,952 B2 | 12/2014 | Ali et al. |
| 8,922,590 B1 | 12/2014 | Luckett, Jr. et al. |
| 8,943,569 B1 | 1/2015 | Luckett, Jr. et al. |
| 8,989,905 B2 | 3/2015 | Sostaric et al. |
| 9,020,431 B2 | 4/2015 | Walker et al. |
| 9,199,391 B2 | 12/2015 | Beaupre et al. |
| 9,207,323 B2 | 12/2015 | Zhu et al. |
| 9,550,312 B2 | 1/2017 | Roberts et al. |
| 11,331,828 B2 | 5/2022 | Goldstein et al. |
| 2004/0252745 A1 * | 12/2004 | Park ................... B28B 23/0031 |
| | | 374/102 |
| 2005/0172861 A1 | 8/2005 | Rich |
| 2007/0116402 A1 | 5/2007 | Slade et al. |
| 2009/0037026 A1 | 2/2009 | Sostaric et al. |
| 2009/0171595 A1 | 7/2009 | Benegas |
| 2011/0029134 A1 * | 2/2011 | Hazrati ................... B28C 7/026 |
| | | 700/265 |
| 2012/0016523 A1 | 1/2012 | Koehler et al. |
| 2013/0289896 A1 | 10/2013 | Cao et al. |
| 2014/0104066 A1 | 4/2014 | Jordan et al. |
| 2014/0104972 A1 | 4/2014 | Roberts et al. |
| 2014/0107844 A1 * | 4/2014 | Koehler ................. B28C 7/026 |
| | | 700/265 |
| 2014/0214715 A1 | 7/2014 | Crocker et al. |
| 2014/0310041 A1 | 10/2014 | Crocker et al. |
| 2014/0316614 A1 | 10/2014 | Newman |
| 2015/0048844 A1 | 2/2015 | Neikirk |
| 2015/0051737 A1 | 2/2015 | Berman |
| 2015/0212061 A1 | 7/2015 | Radjy |
| 2016/0061751 A1 * | 3/2016 | Carr ..................... G01N 27/026 |
| | | 324/637 |
| 2016/0063642 A1 | 3/2016 | Luciani et al. |
| 2016/0107939 A1 | 4/2016 | Monkman |
| 2017/0016874 A1 * | 1/2017 | Radjy ..................... B28C 7/024 |
| 2017/0190619 A1 * | 7/2017 | Crews ..................... C09D 7/43 |
| 2017/0364607 A1 * | 12/2017 | Kaushik ................. C09K 8/00 |
| 2017/0370898 A1 * | 12/2017 | Radjy ..................... G01N 33/38 |
| 2018/0011077 A1 | 1/2018 | Ekinci |
| 2018/0029934 A1 * | 2/2018 | Monkman ............... C04B 22/10 |
| 2019/0008103 A1 * | 1/2019 | Goldberg ............. G05D 1/0246 |
| 2020/0402619 A1 * | 12/2020 | Tregger ................. G16C 20/70 |

FOREIGN PATENT DOCUMENTS

| | | |
|---|---|---|
| CN | 104536456 | 4/2015 |
| JP | 63-60184 A | 3/1988 |
| JP | 10-100117 A | 4/1998 |
| JP | 2006-159658 A | 6/2006 |
| JP | 2007-62263 A | 3/2007 |
| JP | 2011-25426 A | 2/2011 |
| JP | 2019-98707 A | 6/2019 |
| JP | 2019-530597 A | 10/2019 |
| JP | 2020-45758 A | 3/2020 |
| WO | 87/04976 A1 | 8/1987 |
| WO | 2007060272 | 5/2007 |
| WO | 2015073825 | 5/2015 |
| WO | 2017132730 | 8/2017 |
| WO | 2018058012 | 3/2018 |
| WO | 2018190730 | 10/2018 |
| WO | WO-2018190730 A1 * | 10/2018 |

OTHER PUBLICATIONS

TREMCO Roofing and Building Maintenance—SkyBEAM™, 4 pages, 2016.
VOrb IoT for Concrete. Speed up., 1 page.
Jain et al, Machine Vision, pp. 234-248.
Solomon, C. and Breckon, T., Fundamentals of Digital Image Processing: A Practical Approach with Examples in Matlab, pp. 235-259.
Young, Form PCT/ISA/220, International Search Report for PCT/US2020/043920, Dated Oct. 20, 2020, 2 pages.
Young, Form PCT/ISA/237, International Search Report for PCT/US2020/043920, Dated Oct. 20, 2020, 5 pages.
Singaporean communication dated Jul. 21, 2023 in corresponding Singaporean patent application No. 11202200700X.
European communication dated Jul. 5, 2023 in corresponding European patent application No. 20846145.9.
Chinese communication, with English translation, dated Jul. 1, 2023 in corresponding Chinese patent application No. 202080069315.5.
Vietnamese communication, with English translation, dated Feb. 27, 2024 in corresponding Vietnamese patent application No. 1-2022-01252.
Chinese communication, with English translation, dated Mar. 29, 2024 in corresponding Chinese patent application No. 202080069315.5.
Japanese communication, with English translation, dated Jun. 12, 2024 in corresponding Japanese patent application No. 2022-506786.

* cited by examiner

CONCRETE PLACEMENT SENSING USING AERIAL DRONES

This application is a divisional application of U.S. patent application Ser. No. 16/941,494 filed on Jul. 28, 2020, which is allowed and is a Non-Provisional Patent Application claiming the benefit of U.S. Provisional Patent Application Ser. No. 62/881,614 filed on Aug. 1, 2019.

FIELD OF THE INVENTION

The present invention relates to concrete construction processes and systems, and more particularly to coordinating the set time values or value ranges, such as workability or compressive strength windows, of concrete loads delivered to and placed at a job site.

Background of the Invention

The batching of a concrete mix load typically involves introducing cement, aggregates, water, and optional chemical admixtures into the rotatable mixer drums of a ready mix truck wherein the components are mixed uniformly together and transported to a job site, where the concrete mix is placed.

The terms "place" or "pour" may be used hereinafter to refer to various means of conveying plastic concrete from the truck drum to its final resting position at a job site. This includes expelling the concrete from the drum onto a chute from where the concrete can flow or be pushed into a space or formwork for slab, roadway, foundation, wall, or other application; pumping concrete to a location in a high rise building above ground level; spraying the concrete onto a surface, such as a foundation, wall, or tunnel surface; or depositing one concrete mass onto a previously deposited concrete mass, such as in 3D printing processes.

If the concrete is to be used for making a horizontal slab, floor, deck, pavement, or road way, for example, the concrete will have a relatively narrow time period or window within which the concrete can be "finished." Finishing Involves various steps, such as the leveling and smoothing of the surface (troweling) to ensure its durability. The foreperson (or manager) at the building site will want a sense of "initial set time," or, in other words, will want to predict the moment when the poured concrete first develops strength such that it is workable (i.e., the ability to be smoothened or moved into place) and the surface finishing process can be begin. The foreperson will also want to have a sense of the "final set time" or the moment after which the concrete loses workability and can no longer be finished. This is particularly the case when the foreperson does not have a construction crew for each concrete load poured, and limited resources must be marshalled within short time spans.

Determination as to whether poured concrete can be finished (smoothed) is often done by judging the "water sheen" on the concrete surface, but this test is subjective and often distorted by the need to finish quickly. Dusting issues, flaky surface defects, and large scale cracking make it difficult to determine when a concrete surface is ready for finishing. The usual "foot print" test for determining initial or final set time is subjective and prone to error.

If the concrete is be used in a vertical application, such as a wall, column, or supporting structure (e.g., high rise buildings), the concerns of the foreperson could focus on different aspects of set time. Understanding when the concrete begins to develop internal cohesion, leading eventually to increased stiffness and eventually hardness, will help applicators to understand better the proper rate at which the concrete can be pumped or poured to avoid bursting the formwork. Understanding when the concrete begins to acquire compressive strength can enable the foreperson to determine how soon formwork can be removed; or to determine how soon the next concrete section can be cast on top of a previously poured concrete section. Thus, the foreperson might like to understand better the nature of early set time as well as later set time (e.g., compressive strength of concrete at 1, 3, 7, or 28 days after batching).

The present invention focuses upon the determination of one or more set time values or value ranges, such as Initial set time, final set time, and/or two or more set time values. This can involve the beginning and/or end of the workability/finishability window for plastic (workable) concrete; this can also involve strength values for hardened (non-workable) concrete such as compressive strength at 4 hours or at 1, 3, 7, or 28 days, or at other ages.

Contractors at the building site might want to consider one set time value, such as final set time (by which concrete must be finished before hardening); or they might want to consider a set time value range that includes, as another example, both initial set time (after which finishing can begin) and final set time (before which finishing must be completed).

In FIG. 1, the present inventors illustrate a common problem using three example time lines representing three delivery trucks (designated as at 10, 12, and 14) that carry concrete loads in mixer drums. Each load has a different hydration behavior. Each load has a batch time (B) which begins at a batch plant and a different pour time (P) when the load is discharged at the job site. As illustrated by the dotted line rectangle, the problem is caused by different set time values that define different time spans or ranges: e.g., different finishing start times (designated at Fs) and different finishing completion times (designated at Fc). As shown in FIG. 1, concrete poured from trucks 10 and 14 have similar pour (P) times. The finishing crew would be able to finish one poured load 10 before working on poured load 14, as Fc for load 10 ends before Fs for load 14 begins. However, load 12 has a later pour time and a finishing start time (Fs) that occurs later compared to the start time for load 14. Load 12 also has a finishing completion time (Fc) that occurs earlier compared to the finishing time for load 14. Thus, non-coordinated set time behaviors of the concrete pours greatly complicates the finishing process at the job site.

The concrete industry attempts to organize concrete deliveries by batch-loading the trucks at set intervals (e.g., every 15 minutes), but the underlying assumption that the trucks will arrive at similarly spaced intervals at the job site is often challenged. For example, in traveling from the batch plant (B) to pour site (P), trucks can be delayed by traffic and job site congestion, pump failures at the site, admixture dosing errors, temperature changes that affect hydration of concrete at the job site, and other problems. Inconsistency in concrete mixes, such as different batch weights and mix designs (e.g., the load might contain returned concrete) can affect hydration behavior and give rise to set time value variations (e.g., Fs, Fc).

The result of uncontrolled set time values or value ranges in delivered concrete creates expensive and labor-consuming problems, such as concrete sections that must be removed and replaced because they were not finished within the applicable time.

SUMMARY OF THE INVENTION

In surmounting the problems mentioned above, the present invention provides a method for delivering concrete which involves adjusting one or more assigned set time values or value ranges of the concrete mix load being delivered to a job site, preferably based on an assessment of concrete that was previously delivered to and placed at the job site, and to allow delivered concrete to have coordinated set time values or value ranges. This, in turn, allows for control over the properties in the concrete.

As shown in FIG. 2, three concrete loads (B) are delivered in trucks (16, 18, 20) to a job site where they are placed (P) in accordance with an example embodiment of the present invention. In this example, the rheology and hydration rate behavior of the concrete mixes are monitored and adjusted such that post-placement set time value ranges do not overlap. While it is possible to have some overlap (as part of the finishing crew can begin to move from one section of poured concrete to work on the next section), for purposes of simplifying this illustration the finishing start times (Fs) and finishing completion times (Fc) for the three poured concrete loads 16/18/20 are shown as non-overlapping. For example, if one had only a minimal number of crew workers on hand to finish the placed concrete, the Fs and Fc time events could be sufficiently spaced apart so that the crew could finish each poured section (e.g., 16 or 18) before proceeding to the next poured section (e.g., 18 or 20). It is also possible that the set time value ranges could overlap slightly, such as when the foreperson might have some of the finishing crew members move from one poured concrete section to another while completing the necessary finishing before hardening; but the objective is to avoid a number of concrete loads having coinciding set times (e.g., FIG. 1 at 12/14) where one does not have sufficient number of workers to complete the finishing stages.

Hence, the concept of the coordinating set time values or value ranges for the present invention begins with the use of automated concrete rheology (e.g., slump) management system on individual concrete ready-mix delivery trucks, wherein the system is controlled by a processor that that allows for a set time value (e.g., initial set time) or value range (e.g., initial and final set time values, and/or strength level) to be inputted into or calculated (e.g., by processor of slump monitoring system on board a concrete delivery truck).

The invention also allows for adjustment of the initial set time based on concrete rheology data, such as by the foreperson at the site, or such as based on information from other concrete delivery trucks which are monitoring various concrete loads delivered to the job site, or perhaps even based on sensor data obtained from sensors positioned above or on the surface of the placed concrete or embedded within the placed concrete (or a combination of these).

For purposes of the present invention, the concept "set time value or value ranges" may refer to any number of activities, including: (a) initiation of finishing; (b) completion of finishing; (c) removing formwork or mold from concrete (i.e., after it hardens); (d) allowing foot or car traffic upon the concrete; (e) casting further concrete on top of the poured concrete; or other pour site activities, such as (f) pre-stress concrete mechanism adjustments. The set time value will be presumed to start from the moment that the concrete load has been loaded or mixed at the batch plant, or otherwise readjusted (if it is returned from a different job site or even from a different pour location at the same job site) to reflect the moment that fresh concrete is batched on top of the returned concrete load. In other words, the set time value or value ranges can cover any of a number time of placement time events or even post-placement properties, such as concrete compressive strength at various ages, depending upon application.

Thus, an exemplary method of the present invention for coordinating delivery of concrete, comprises:

(A) providing at least two delivery trucks, each having a mixer drum containing a concrete load and a processor-controlled system for monitoring rheology (e.g., slump, slump flow, yield stress) and at least one set time value or value range (e.g., initial set time, final set time, compressive strength, or mixtures of these values) of the concrete load in the drum, the processors programmed to perform functions comprising:

(i) accessing at least one stored set time value or value range assigned to concrete loaded in the mixer drum for delivery to a job site;

(ii) calculating at least one current set time value or value range for the load based on monitored hydration over time; and (iii) comparing the at least one stored set time values or value ranges with the calculated at least one current set time values or value ranges; and (B) adjusting current set time value(s) or value range(s) by introducing a set accelerator, set retarder, or mixture thereof into at least one of the at least two delivery truck concrete loads to effectuate or to modify the sequential placement, finishing, demolding, formwork removal, or compressive strength phases of the concrete loads poured from the at least two delivery trucks.

In further exemplary embodiments, stored or current set time values could include initial set time (after which finishing may begin), final set time (before which finishing should be completed); and perhaps even a set time value range (e.g., defined by both initial and final set times); and it could also include other placement events (e.g., the development of strength of poured concrete at one or more concrete ages, e.g., at 4 hours, 4 days, or other ages from time of batching). Again, there can be some overlap in terms of workability windows (e.g., the end time for a prior pour might occur after the start time for subsequent pour). Set time values whether stored or current can be established, for example, by monitoring of temperature changes in the concrete over time, preferably at given concrete slumps, using commercially available slump monitoring systems onboard the delivery truck. The present inventors envision that adjustment of current set time value or value range for the concrete loads may be accomplished by administering doses of set accelerator, set retarder, or mixtures thereof, using such commercially available monitoring systems (e.g., VERIFI® Monitoring Systems from GCP Applied Technologies Inc. of Cambridge, Mass.). Moreover, in further example embodiments, the first job site might not be the eventual "pour site," as the present invention facilitates re-routing of full or partial delivery truck loads from a first job site to another job site to deliver a full or partial load.

In further example embodiments, the monitoring of hydration of each concrete load over time can be done a number of ways. For example, the temperature of the concrete load can be measured over time and taken into consideration along with the batch amount (including load size at the batch plant and any additional water or admixture added at any time, and additionally Including the age of the concrete).

The present invention also provides a method for monitoring set time conditions of a plurality of concrete placements, which comprises:

moving over a plurality of concrete placement locations at a job site at least one aerial drone having at least one sensor for monitoring hydration over time of the placed concrete (e.g., sensors chosen from optical, infrared, acoustic, radio wave, microwave, electrical resistivity, electrical capacitance, and ultrasonic sensors) to obtain data signals indicative of hydration;

comparing the obtained data signals with previously stored data signals to obtain set time values or value ranges correlated with the hydration over time data obtained from the at least one sensor; and generating a pictorial diagram or map of the plurality of concrete placement locations along with set time values or value ranges, or suggested sequence priorities based on set time values or value ranges, thereby to provide indication of placements that are amenable to sequential treatment with respect to (a) initiation of finishing; (b) completion of finishing; (c) removing formwork or mold from the concrete; (d) allowing foot traffic or car traffic on the concrete; (e) releasing tensioned cables from jacks (e.g., such as used in pre-stressed concrete applications); (f) anchoring or grouting post-tensioned cables (e.g., such as for post-tensioned concrete); or (g) casting further concrete on top of previously poured concrete.

Further advantages and features of the invention are described in further detail hereinafter.

BRIEF DESCRIPTION OF DRAWINGS

An appreciation of the benefits and features of the invention may be more readily comprehended when the following written description of preferred embodiments is considered in conjunction with the drawings, wherein.

DETAILED DESCRIPTION OF EXEMPLARY EMBODIMENTS

As used in the specification, various devices and parts may be described as "comprising" other components. The terms "comprise(s)," "include(s)," "having," "has," "can," "contain(s)," and variants thereof, as used herein, are intended to be open-ended transitional phrases, terms, or words that do not preclude the possibility of additional components.

The term "concrete" typically refers to a mixture of cement (which often contains supplementary cementitious materials such as limestone, fly ash, granulated blast furnace slag and other pozzolanic materials) and aggregates (e.g., fine aggregate such as sand, coarse aggregate such as gravel) and optionally one or more chemical admixtures (e.g., plasticizers for increasing workability, set accelerators, set retarders, air entrainers, air detrainers, plastic shrinkage reducing admixtures, corrosion inhibitors (for rebar) for modifying concrete in its plastic or hardened state. Concrete is considered to be hydratable material in that the addition of water into the mixture of cement and aggregates initiates a hardening reaction.

The term "cement" includes hydratable cement such as Portland cement which is produced by pulverizing clinker consisting of hydraulic calcium silicates, aluminates and aluminoferrites, and one or more forms of calcium sulfate (e.g., gypsum) as an interground additive. Typically, Portland cement is combined with one or more supplemental cementitious materials, such as fly ash, granulated blast furnace slag, limestone, natural pozzolans, or mixtures thereof, and provided as a blend, all of which binds aggregates together to make concrete. Thus, "cement" and "cement binder" may also include supplemental cementitious materials which have been inter-ground with Portland cement during manufacture.

The term "concrete delivery truck(s)," also known as ready-mix concrete truck(s), shall mean and refer to a vehicle having a rotatable mixer drum with non-vertical axis of rotation. Such mixer drums typically have at least one blade or fin mounted on the inner wall of the drum and arranged spirally around the axis of rotation, such that rotation of the drum in one direction forces concrete components towards a closed end of the drum (thus, in a mixing or loading mode); while rotation in the opposite direction expels materials through the open end of the drum (thus, in a pouring or expelling mode).

Figure 1:
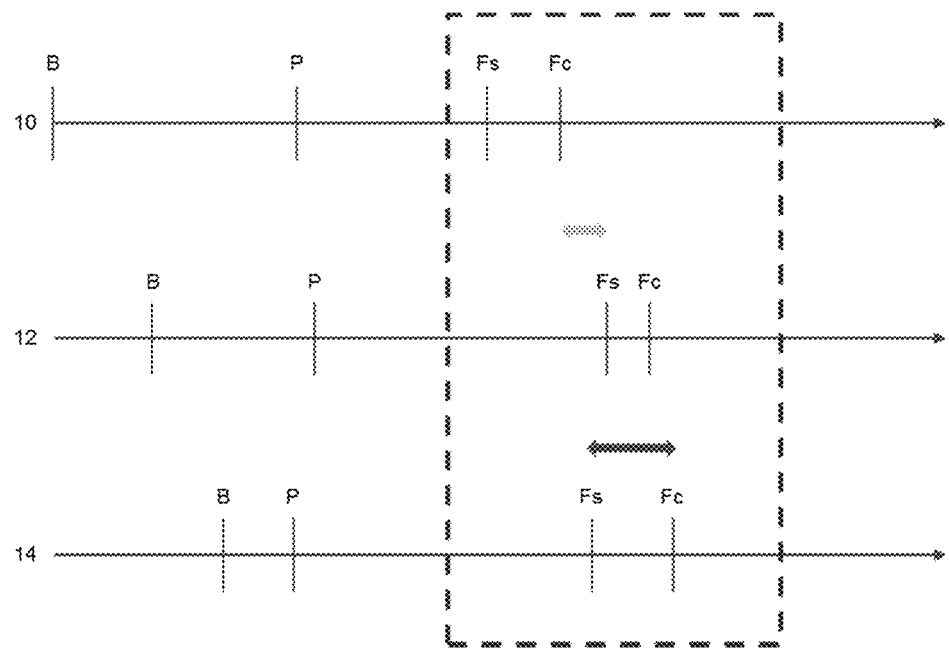
FIG. 1 is an illustration of an example timeline of three ready-mix delivery trucks having concrete loads wherein hydration states are not coordinated, as explained in the Background Section above.
Figure 2:
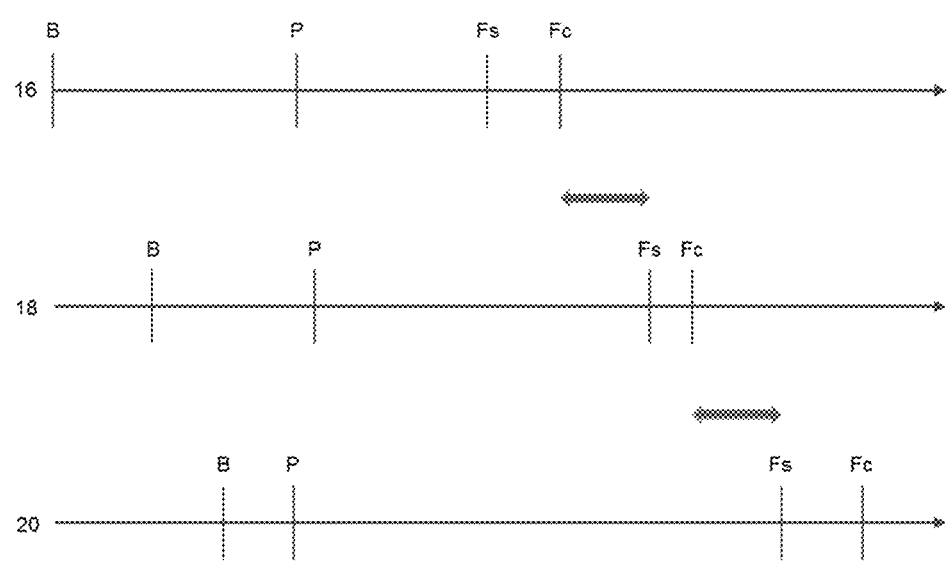
FIG. 2 is an illustration of an example timeline for ready-mix delivery trucks having concrete loads wherein hydration states are coordinated using exemplary methods of the present invention, as explained in the Summary Section above.

The phrase "batch time" or "batching time" is designated as "B" in FIGS. 1 and 2 and is used to refer to various events, including, for example: (a) the time at which the truck begins to receive concrete or certain mix components for making concrete (e.g., cement, aggregates, water, optional chemical admixtures) into the mixer drum; (b) the time at which one or more chemical admixtures (e.g., superplasticizer, set retarder, set accelerator, or mixtures thereof) are added into the mixer drum containing concrete or concrete components; (c) the time at which the materials have been mixed together in the mixer drum and determined to be uniformly mixed (e.g., such as may be determined by confirming that slump sensor readings are relatively constant over a predefined number of drum rotations); or (d) the time at which the truck leaves the batch plant.

For example, a particular batch plant might customarily indicate the time at which components were introduced into the mixer drum, and this could be documented or memorialized in the electronic or paper batch ticket; and, if an electronic batch ticketing is issued, the time could be transmitted to a dispatch center and/or the automated slump monitoring system of the delivery truck into which the concrete was loaded, and this could be used to determine set time value or value ranges for the particular load.

The term "pour" means or refers to when a full or partial load of concrete is poured, sprayed, or otherwise deposited into final resting position at the job site. Multiple pours can occur. For example, an initial pour may be done to check the concrete properties. Adjustments can be made to the concrete which can continue to be poured. Partial pours may occur if the receptacle for receiving the concrete is full, or, if after checking the concrete properties, the load is to be rejected. In these cases, the concrete may be returned to a batch plant, or to another location on the same or different job site, so that the remaining concrete can be used.

For purposes of FIGS. 1 and 2, the "pour" is designated as "P" and refers to the moment when a full or partial load of concrete expelled from a delivery truck at a job site. One truck can have multiple pours. For example, an initial pour may be done to check the concrete properties, and to permit adjustments to be made to the concrete, so that remaining portions of a given load can be expelled from the truck into position.

Partial pours may also occur if the formwork, mold, or pump hopper for receiving the concrete mix is full. As another example, partial pours can occur if the particular load is rejected; and the rejected concrete may be returned to a batch plant or to another location on the same or different job site where he remaining concrete is put to use.

The meaning of the concept "set time value or value ranges" as used herein and above will depend upon the particular application for a given concrete load. The concept may encompass only a single moment in time (e.g., final set) or it can comprehend a time period (e.g., both initial set and final set) as calculated from batching (or reconditioning of returned concrete). Thus, exemplary time set values or value ranges may include the moment or period in time for any one or more of the following activities: (a) initiation of finishing; (b) completion of finishing; (c) removal of formwork from or demolding of concrete; (d) allowing foot or car traffic upon the concrete; (e) releasing tensioned cables from jacks (as used in pre-stressed concrete applications); (f) anchoring or grouting of post-tensioned cables (as for post-tensioned concrete); or (g) casting further concrete on top of previously poured concrete.

As explained above, for horizontal applications (such as pouring a concrete highway, slab, floor, etc.), the set time values of likely interest would include "initial set time," or, in other words, the earliest time (after batching or reconditioning of the concrete) at which pushing, leveling, screeding, smoothing, or texturing of the concrete surface by trowel or other finishing tool can begin (See e.g., ACI 302.1R-15). When the concrete becomes too stiff for finishing, this is sometimes referred to as "final set time," a term which can also be used to refer to the point in time after which formwork or mold can be removed. See e.g., ASTM C191-18a, ASTM C266-18, ASTM C807-18, and ASTM C403-16.

Other set time values or value range might include, as another example, the initial set time and/or final set time, with a post-pour concrete property such as compressive strength. In some highway slab projects, it has been desired to achieve a certain compressive strength target (400 psi) within a given period of time (e.g., 4 hours). Again, the set time value or value ranges that one might desire to monitor and to adjust in the concrete load will depend upon the specific application in which the concrete load will be used.

As another example, for pre-stressed concrete applications, in which steel wires, cables, or rods are used for pre-stressing the concrete, the set time value or value range can include the earliest time (from batching) for anchoring or grouting the cables in the concrete, and/or for releasing tensioned cables from jacks.

The term "assigning" or "inputting" as used herein will refer to the set time value or value range that is entered into a processor for monitoring and/or adjusting the concrete load, and this could include, for example, the processor-controlled concrete monitoring system that monitors rheology (e.g., slump or slump flow) of the concrete mix load contained in the delivery truck drum. As mentioned above, this set time value or value range can be derived from an electronic ticket provided by the concrete batch manufacturer (e.g., many batch plants simply use 15-minute intervals as batching times, whereby the delivery truck drives under a feeder system that loads cement, sand/rocks, and water into the mixer drum and optional chemical admixture(s). Alternatively, set time value(s) or value range(s) can be calculated by an onboard (truck) processor based on rheology (or slump or slump flow) or other factors by the processor.

It is contemplated by the present inventors that the exemplary methods and systems of the present invention can be carried out using automated slump management (monitoring) systems that are commercialized by GCP Applied Technologies Inc. through its affiliate Verifi, LLC, both of Cambridge, Mass., USA. Such concrete monitoring systems enable one to manage the slump or other rheological properties (e.g. slump flow, yield stress, viscosity) during in-transit delivery of the concrete from batch plant to jobsite where the concrete Is placed. The patent literature describes various automated process-controlled concrete monitoring systems. Such systems can be configured and/or programmed to monitor rheology and various other concrete properties, and to deliver admixtures into the mix load. See e.g., U.S. Pat. Nos. 8,020,431; 8,118,473; 8,311,678; 8,491, 717; 8,727,604; 8,764,273; 8,989,905; as well as U.S. Ser. No. 11/834,002 (Publ. No. US 2009/0037026 A1); U.S. Ser. No. 14/052,289 (Publ. No. 2012/0016523 A1); U.S. Ser. No. 14/052,289 (Publ. No. 2014/0104066 A1); U.S. Ser. No. 14/052,310 (Publ. No. 2014/0104972); PCT/US2015/025054 (Publ. No. WO 2015/160610 A1); and PCT/US2014/065709 (Publ. No. WO2015073825 A1), incorporated by reference herein.

It is further believed that other sensors, such as force sensors (which employ stress or strain gauges), can be used to monitor the slump of concrete in the truck mixer drum. See e.g., U.S. Pat. No. 8,848,061 and US Publication No. 2015/0051737 A1 of Berman (Sensocrete Inc./GCP Applied Technologies), U.S. Pat. No. 9,199,391 of Denis Beaupre et al. (I. B. B. Rheologie Inc.), or US Publication No. 2009/0171595 and WO 2007/060272 of Benegas.

While automated concrete monitoring systems are used customarily for monitoring "slump," it will be understood that the present invention includes monitoring of other rheology parameters such as slump flow, yield stress, viscosity, and other rheological parameters. The specific term "slump" is employed as a matter of convenience.

An assigned or inputted set time value or value range, as previously discussed, can be revised by the use of automated concrete monitoring systems based on data analyzed by the system processor. Such data can include data obtained from electronic sensors used at the job site, for example, to obtain moisture, humidity, temperature, or other properties. Data can also be obtained from the concrete monitoring system used on another (e.g., lead) truck previously delivering concrete at the same pour site, and such data could include slump, temperature, water content, mix or batch proportions, or other Information stored or derived by the onboard monitoring system.

In various exemplary embodiments, the revision of assigned or inputted set time values can be undertaken by the management system processor based on sensor data obtained from sensors that are used for monitoring one or more properties of the concrete after it is placed (i.e., poured, cast, screed, leveled, smoothened, etc.) at the job site.

Sensors Positioned Above or at Concrete Surface.

The present inventors envision that one or more moveable or portable sensors may be used for monitoring the surface of concrete once it is poured into place. For example, one or more sensors can be used in "unmanned aerial vehicles" (UAV) or drones, as explained further in the following paragraphs, or can be suspended on hand-held poles, or suspended using cables or pulley assemblies that can be moved over a slab, patch, or other segment of poured concrete. As another example, one or more sensors can be used in nozzles for spraying, injecting, or depositing concrete (e.g., shotcrete, injecting concrete into mines, depositing concrete such as in 3D printing processes). The type of sensors that can be used may be chosen from optical, infrared, acoustic, radio wave, microwave, electrical resistivity, electrical capacitance, and ultrasonic sensors, and other sensor types, all of which are types of sensors known for measuring a property of concrete while in its plastic and/or hardened state.

Sensors on Drones.

The phrase "unmanned aerial vehicle" (UAV), or drone, refers to devices that can be flown by remote control and that can carry one or more sensors for monitoring concrete placements at a job site and a wireless transmitter for sending data signals to a processor, such as a processor onboard the concrete delivery truck, that communicates with one or more processors in the cloud, on one or more other delivery trucks, and/or on one or more portable devices, including smart phones, tablets, or other portable devices at the job site. For example, in U.S. Pat. No. 8,599,646, Parrot describes the use of drones having ultrasonic telemetry devices to measure distances and topography without interference from neighboring drone signals. In U.S. Ser. No. 13/998,871, Newman describes a data collection system to enable drones to collect image data, process the data for anomalies, and pair the images to physical locations. U.S. application Ser. No. 14/843,455 (MetLife) describes the use of drones to collect sensor data, convert the data into insurance related information and transmit the data information through wireless communication. There have also been improvements which can enable the use of drones in difficult areas. U.S. Pat. No. 8,874,283 describes methods to enable drones to be utilized in enclosed spaces and controlled with or without line of sight to the drone, which can be advantageous at a construction site.

In the construction field, drones have found use primarily in enabling digitization and visualization of construction sites (see, e.g. CN 104536456A). They have been used to capture aerial images that can be presented to contractors or other site planners (See e.g., TREMCO SkyWEAM™ Asset Mapping). In US 2017/0016874A1, it was disclosed that drones can harvest data signals from sensors embedded in concrete at a construction site.

Sensors Embedded Within Concrete.

In exemplary embodiments of the invention, embeddable sensors may be employed. These are placed into the matrix of the poured concrete, or tied onto rebar before the concrete is poured into a mold or formwork, and transmit data corresponding to the humidity, temperature, hardening, and other properties of placed concrete, through wired or wireless means. For example, embedded sensors have been used in concrete structures for structural monitoring, See e.g. U.S. Pat. Nos. 4,943,930, 8,913,952); strength development, See e.g. U.S. Pat. No. 7,551,085; humidity measurement, See e.g. US Publ. No. 2007/0116402; as well as other applications, including corrosion detection, See e.g. US Publ. No. 2015/0048844. Sensors have even been envisioned to be placed inside plastic concrete contained in concrete delivery trucks, See e.g., US Publ. No. 2015/0212061, and are intended for monitoring properties such slump, temperature, and humidity among others. These sensors can remain in the concrete as it is poured and provide, for example, temperature readings that can be used for prediction of strength evolution of a hardening concrete slab. A number of commercially available sensors can be embedded in concrete and generate signals indicating or corresponding to the temperatures and/or humidity state(s) of the concrete. These include Giatec of Canada (SMARTROCK™ and BLUEROCK2™ sensors), Concrete Sensors Co. of Cambridge, Mass. (NO- VOCRETE™ sensors); MATOlog of Finland (e.g., CURE™ sensors); Wake Inc. of Grandville, Mich., (HARDTRACK™ sensors); Quadrel LLC of Pittsburgh, Pa. (vOrb™ sensors); Flir of Wilsonville, Oreg. (INTELL-ROCK™ sensors); and AOMS of Canada (LUMICON™ sensors).

Many of the above-mentioned sensors measure humidity through electrical resistivity or capacitance measurements and include a thermocouple and/or piezo electric sensor for measuring temperature, and they transmit data signals wirelessly to handheld devices, remote processors, and/or the cloud for real time monitoring and logging of temperature, humidity, and other maturity data. The signal data of sensors such as these can be correlated with one or more physical properties (e.g., compressive strength at various times after batching) and used by system processor of slump monitoring system to adjust a current concrete load, such as by introducing one or more set accelerator, set retarder, or mixture of both, into the concrete.

Some of the sensors mentioned in the foregoing section which can be embedded in concrete may also be used when positioned against or disposed upon the surface of the concrete. For example, one or more sensors can be fastened to formwork or molds against or into which the concrete is cast; or tied or fastened to rebar, cladding, tunnel wall, foundation, or other structure against which concrete is cast or sprayed.

Various exemplary embodiments of the invention, with some further exemplary aspects for these various embodiments, are set forth below.

In a first example embodiment, the invention provides a method for coordinating delivery of concrete, comprising:

(A) providing at least two delivery trucks, each having a mixer drum containing a concrete load and a processor-controlled system for monitoring rheology (e.g., slump, slump flow, yield stress) and at least one set time value or value range (e.g., initial set time, final set time, compressive strength, or a combination of these or other values) of the concrete load in the drum, the processors programmed to perform functions comprising:
  i. accessing at least one stored set time value or value range assigned to concrete loaded in the mixer drum for delivery to a job site;
  ii. calculating at least one current set time value or value range for the concrete load based on monitored hydration over time; and
  iii. comparing the at least one stored set time values or value ranges with the calculated at least one current set time values or value ranges; and
(B) adjusting current set time value(s) or value range(s) by Introducing a set accelerator, set retarder, or mixture thereof into at least one of the at least two delivery truck concrete loads to effectuate or to modify the sequential placement, finishing, demolding, formwork removal, or compressive strength phases of the concrete loads poured from the at least two delivery trucks.

In a first aspect of this first example embodiment, the system for monitoring rheology (e.g., slump) can be based on the use of one or more hydraulic pressure sensors (See e.g., U.S. Pat. No. 8,818,561 regarding sensors on both charge pressure port and discharge pressure port), force sensors (e.g., strain or stress gauge), acoustic sensors, or a combination of these. Various known rheology monitoring systems were previously described above. Particularly preferred monitoring systems are based on hydraulic pressure sensor(s) in combination with drum rotation speed monitors (e.g., gyroscopes, accelerometers on drum, or both). Set time value or value ranges, whether stored or current, can be generated for example through monitoring of temperature change over time of the concrete load, preferably at given concrete slumps, using an automated slump monitoring system. The monitoring of concrete load over time can be done a number of ways. For example, the temperature of the concrete load can be measured over time and taken into consideration along with the batch amount (including load size at the batch plant and any additional water or admixture added at any time, and additionally including the age of the concrete). The concrete loads after pouring at the job site have set time values or value ranges which preferably do not coincide although there could be some overlap. In other exemplary aspects, the first job site might not be the eventual "pour site" where a truck is re-routed to travel from a first job site to another job site to deliver a full or partial load. Adjustment of current set time value or value range for the concrete load may be accomplished, for example, by administering doses of set accelerator, set retarder, or mixtures thereof.

In second aspect of the first example embodiment, the phrase appearing above in Section A(ii) involving "calculating at least one current set time value or value range for the concrete load based on monitored hydration over time" can involve one of many known ways for tracking the hydration of the concrete of time, including, in addition to tracking temperature changes or the rate of temperature changes, the water content, slump change, or other known means of tracking hydration states. It is preferable for such tracking to include information regarding the amount of cementitious material originally batched along with the concrete components in the mixer drum, and this can be obtained from the ticket Issued by the batch plant.

In a third aspect of the first example embodiment, at least two of the at least two concrete delivery trucks are bearing concrete loads originating from different batch plants.

In a second example embodiment, which can be based on the first example embodiment described above, the invention provides a method wherein, in step (A), at least three delivery trucks (and more preferably at least six trucks) are provided, each having a mixer drum containing a concrete load and a processor-controlled system for monitoring rheology and set time value or value range of the concrete load in the drum, the processors programmed to perform functions (i), (ii), and (III) as previously described; and each of the at least three delivery trucks (and more preferably at least six trucks) adjust the stored set time value or value range or the current set time value or value range of the concrete loads.

In a third example embodiment, which can be based on the first or second example embodiment above, the invention provides a method wherein both the stored set time value or value range and the current set time value or value range are adjusted.

In a fourth example embodiment, which can be based on any of the first through third example embodiments above, the invention provides a method wherein the stored set time value or value range is calculated based on factors which include the estimated age of the concrete at pour time. The estimated age may be calculated based, for example, on traffic, job site conditions, or other factors.

In a fifth example embodiment, which can be based on any of the first through fourth example embodiments above, the invention provides a method wherein set time values or value ranges are chosen from time values for (a) initiation of finishing; (b) completion of finishing; (c) removing formwork or mold from the concrete; (d) allowing foot traffic or car traffic on the concrete; (e) releasing tensioned cables from jacks (as used in pre-stressed concrete applications); (f) anchoring or grouting post-tensioned cables (as for post-tensioned concrete); or (g) casting further concrete on top of previously poured concrete.

In a sixth example embodiment, which can be based on any of the first through fifth example embodiments above, the invention provides a method wherein the stored set time value or value range accessed by, or accessed and adjusted by, at least one of the delivery truck processor-controlled systems Is derived from (a) ticket information provided by a batch plant which sourced the concrete in the truck mixer drum (e.g., the ticket information may include mix design, material batch weights, concrete load volume, water content or water/cement ratio, or combination thereof); (b) foreperson at job site where concrete from the truck mixer drum is to be poured (e.g., the foreperson could take into consideration job-site conditions including but not limited to ambient temperature, relative humidity, wind speed, UV index, traffic congestion, worker conditions, etc.); (c) a processor that receives data signals from humidity, moisture, and/or temperature sensors embedded within, positioned against the surface of, or embedded within concrete poured or placed at the job site or another job site (or a combination of such sensors); or (d) a processor monitoring of another concrete delivery truck having a processor-controlled system for monitoring rheology and set time value or value range of the concrete load (e.g., the lead delivery truck or other delivery truck pouring concrete at the job site having an earlier set time value or value range).

In a first aspect of the sixth example embodiment, a humidity, moisture, and/or temperature sensor can embedded within and/or placed on the surface of the poured concrete.

In a second aspect of the sixth example embodiment, one or more sensors can be suspended above poured concrete at the job site using aerial drones, cables, poles, or other suspension means. Preferred sensors for this application may be chosen from optical, infrared, acoustic, radio wave, microwave, electrical resistivity, electrical capacitance, and ultrasonic sensors, or combinations thereof. These sensors can provide data signals indicative of hydration state or rate of the concrete, and such data signals can be transmitted, preferably wirelessly, so that the system processor on board the delivery truck can monitor the current hydration state of the concrete load, and can record and store the information so that it can be used later as historical (stored) information and correlated with a target set time value or value range.

In a third aspect of the sixth example embodiment, sensors (e.g., conductivity, ultrasonic) can be used inside hoses for injecting or depositing concrete at the job site, such as in nozzle or hoses used for spray-application of shotcrete, nozzles for depositing concrete in a 3D printing process, or for expelling concrete sections such as for making tunnels or precast concrete shapes.

In a seventh example embodiment, which can be based on any of the first through sixth example embodiments above, the invention provides a method further comprising adjusting the at least one stored set time value or value range, and providing a report or indication of adjustments made to the at least one stored set time value or value range. In a first aspect of this example, the monitoring system of the delivery truck will use at least one stored set time value or value range, e.g., initial set time, final set time, time for removing formwork from the concrete, and will be able to adjust the store values or value ranges based on new data information, such as obtained as described in the sixth example embodiment above. Thus, the foreperson at the job site where the concrete Is to be poured (or sprayed or otherwise placed) can send Instructions to the processor to add 5 or 10 minutes to the set time due to a delay at the job site. As another example, a remote processor or even the processor used for monitoring a delivery truck concrete load can receive data signals or other information derived from sensors embedded in or positioned above or against concrete that was previously poured, and make adjustments to the stored set time values so that the truck system processor can used the revised values to make adjustments to the current set time value of the concrete load in the truck. In further examples, the system will enable a record or confirmation of the adjustments made to the stored set time value or value range.

In a second aspect of this example embodiment, adjustments to the stored set time value can be sent to or retrieved by the concrete monitoring systems on other concrete delivery trucks and used for coordination of pouring and finishing events at the pour site.

In an eighth example embodiment, which can be based on any of the first through seventh example embodiments above, the invention provides a method wherein the current set time value or value range is compared to stored set time value or value range in terms of at least one factor chosen from temperature of concrete, rate of temperature change in the concrete, batch amounts or mix design of the concrete, adjustments in water or admixture (e.g., cement dispersant, chemical plasticizing or superplasticizing admixture) added into the concrete load, rheology (e.g., slump, slump flow, yield stress), or other property of the concrete In a ninth example embodiment, which can be based on any of the first through eighth example embodiments above, the invention provides a method wherein at least one of the concrete loads in one of the at least two delivery trucks is returned concrete (e.g., returned from the same or different job site, optionally but likely to contain set retarder admixture that was administered into the partial remaining load in the mixer drum), and further wherein the comparison of stored and current set time values or value ranges includes consideration of the age of concrete from the initial batching of the concrete which was returned from the job site.

In a tenth example embodiment, which can be based on any of the first through ninth example embodiments above, the invention provides a method wherein a first concrete load from a first delivery truck is poured into place, and a second concrete load from a second delivery truck is poured on top of the first concrete load while the first concrete load is in a plastic state, and wherein the first load and second load have overlapping set time values or value ranges.

For example, in U.S. Pat. No. 7,968,178, Scurto et al. disclosed that a first slab of concrete could be cast onto a first concrete slab while it was still in a somewhat plastic state, so as to create an integrated region between the successively cast slabs. In this manner, the present invention can permit set time values or set time value ranges, as between successive or nearby concrete load deliveries at a job site, to be slightly overlapping, so as to facilitate bonding between concrete that is poured, sprayed, printed, deposited, or otherwise placed onto previous concrete that is still in a plastic state. In the construction industry, one may hear a contractor speak about casting a "first lift" (e.g., first concrete mass or structure), and then casting a "second lift" on top of the first one. This is frequently related to the casting self-consolidating or self-compacting concrete. Although the concrete, due to its fluidity, can be cast quickly, the fluid concrete can Impart a great force on formwork, increasing the risk of "blow-outs" where the formwork catastrophically fails. Based on coordinated set times, the fluid concrete can be left to stiffen, where the next "lift" can be cast safely upon it.

In an eleventh example embodiment, which can be based on any of the first through tenth example embodiments above, the invention provides a method wherein the stored set time value or value range for concrete previously delivered and placed at the job site is obtained or derived from data signals generated by at least one sensor in the nozzle, hose, or other conduit of concrete during deposition or spraying of the concrete through the nozzle, hose, or conduit at a job site. For example, the sensor could be an electrical conductivity sensor (or two electrodes spaced apart within the nozzle and/or hose so that a current can be sent through the electrodes and conductivity of the concrete can be measured); or the sensor could be of the type of sensors (e.g., infrared (IR), ultrasonic) previously mentioned above.

In a twelfth example embodiment, which can be based on any of the first through eleventh example embodiments above, the invention provides a method wherein a portion of the concrete load in at least one of the delivery trucks is poured at a first job site, and, within fifteen minutes and more preferably within ten minutes of the pour, a dose of set retarding agent is introduced into the remaining portion of the concrete load in the delivery truck, and the remaining portion is transported by the delivery truck to a second job site and poured into place at the second job site. In further aspects of this example, at least one subsequent dose of set retarding agent is administered into the remaining portion of the concrete load during transit from the first job site to the second job site.

In a thirteenth example embodiment, which can be based on any of the first through twelfth example embodiments above, the invention provides a method wherein at least five (and more preferably at least ten) delivery trucks are provided in accordance with step (A) having concrete loads whose set time values or value ranges are adjusted in accordance with step (B), said adjustments being made using set time value or value range calculations based on signal data obtained or derived from at least one sensor for monitoring hydration over time of placed concrete at the job site.

In a first aspect of this thirteen example embodiment, the hydration over time signal data for a plurality of concrete placement locations at a job site is generated by at least one sensor chosen from optical, infrared, acoustic, radio wave, microwave, electrical resistivity, electrical capacitance, and ultrasonic sensors, and the at least one sensor is preferably moved over the concrete placement locations using an aerial drone. A processor, such as the one used for monitoring rheology of the truck concrete load can be programed to compared the obtained data signals with previously stored data signals to obtain set time values or value ranges correlated with the hydration over time data obtained from the at least one sensor; and, in further exemplary embodiments, a processor, such as a personal computer, lap top, or hand-held smart phone or smart watch can be used to generate a pictorial diagram or map of the plurality of concrete placement locations along with set time values or value ranges, or suggested sequence priorities based on set time values or value ranges, thereby to provide indication of placements that are amenable to sequential treatment with respect to (a) Initiation of finishing; (b) completion of finishing; (c) removing formwork or mold from the concrete; (d) allowing foot traffic or car traffic on the concrete; (e) releasing tensioned cables from jacks (e.g., such as used in pre-stressed concrete applications); (f) anchoring or grouting post-tensioned cables (e.g., such as for post-tensioned concrete); or (g) casting further concrete on top of previously poured concrete.

In a second aspect, the hydration state of various placed concrete sections can be Indicated on a visual monitor in terms of darkened section, or other visual aids, corresponding in darkness with state of hydration.

In a fourteenth example embodiment, which can be based on any of the first through thirteenth example embodiments above, the invention provides a method for monitoring set time conditions of placed concrete loads, the method comprising:

moving over a plurality of concrete placement locations at a job site at least one aerial drone having at least one sensor for monitoring hydration over time of the placed concrete (e.g., sensors chosen from optical, infrared, acoustic, radio wave, microwave, electrical resistivity, electrical capacitance, and ultrasonic sensors) to obtain data signals indicative of hydration;

comparing the obtained data signals with previously stored data signals to obtain set time values or value ranges correlated with the hydration over time data obtained from the at least one sensor; and generating a pictorial diagram or map of the plurality of concrete placement locations along with set time values or value ranges, or suggested sequence priorities based on set time values or value ranges, thereby to provide indication of placements that are amenable to sequential treatment with respect to (a) initiation of finishing; (b) completion of finishing; (c) removing formwork or mold from the concrete; (d) allowing foot traffic or car traffic on the concrete; (e) releasing tensioned cables from jacks (e.g., such as used in pre-stressed concrete applications); (f) anchoring or grouting post-tensioned cables (e.g., such as for post-tensioned concrete); or (g) casting further concrete on top of previously poured concrete.

In a first aspect of this fourteenth example embodiment, the pictorial diagram or map can be generated on a hand-held device, or, as another example, on goggles worn by a site foreperson. The pictorial diagram may, for example, be a picture or image of concrete delivery trucks as viewed on a pour site map, and allow for digital values and/or colors to be overlaid upon the truck images or concrete segment images. Thus, a site foreperson could direct delivery trucks to get into line for pouring, or to pour, according to visual Information as to pour status (i.e., set time value); and/or could direct finishing crew to those segments of poured concrete which have necessary setting values or characteristics.

Figure 3:
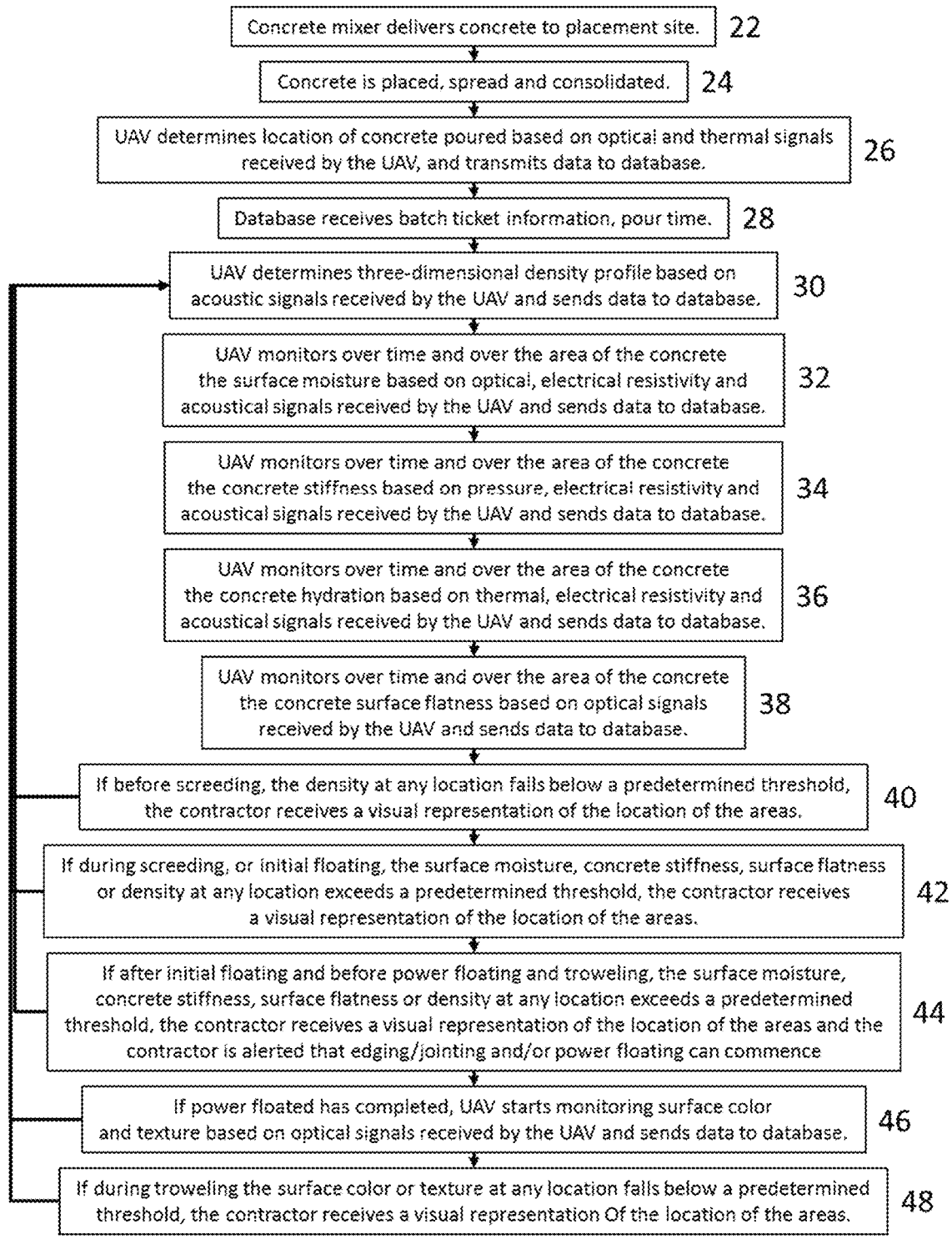
FIG. 3 is a block diagram describing use of a UAV (aerial drone having sensor) to monitor concrete setting status at a job site in accordance with certain embodiments of the present invention.

FIG. 3 is a block diagram which illustrates an exemplary process in accordance with certain embodiments of the Invention. First, concrete is delivered to the placement site (block 22) and then poured, spread, and consolidated (block 24). For each concrete delivery truck load (or group of concrete delivery truck loads) of concrete thus placed, an UAV (or fleet of UAVs) can determine one or more perimeters of the placed concrete using telemetry based on optical and thermal signals (block 26). For example, the color difference (determined from comparing sequential images), or the heat signature from the concrete, can delineate the poured concrete from form edges or pre-placed concrete, as the formwork and concrete typically have different temperatures. Alternatively, image analysis comparing before and after pouring can also help determine a perimeter of the placed concrete. Using this information, a processor-accessible database can be uploaded with, for example, the identification of the concrete delivery truck (e.g., concrete delivery truck number) that delivered the concrete, the batch ticket (containing the concrete constituents or mix design, e.g. water content), the time the concrete was poured, and the location of the concrete. This Information can help determine if all sections of the mold are properly filled, and if not, the contractor can be alerted to vibrate and add more concrete.

Also as shown in FIG. 3, the concrete article can be monitored for different properties (blocks 30, 32, 35, 36 and 38). For example, the UAV can scan the poured concrete article for differences in density that might Indicate consolidation issues to be addressed before the concrete hardens. Available technologies that may be used by the UAV to carry this out include nuclear density gauges, ground penetrating radar, or capacitance energy dissipation (See, e.g. U.S. Pat. No. 5,952,561). The present inventors also envision that air-coupled surface wave measurements can be employed in the present invention (See e.g., US Publication No. 2013/0289896). If differences in density are discovered (block 40), the affected areas can be relayed to the contractor by, for example, a mobile application so that the contractor can visually see where consolidation needs to be addressed through further compaction or vibration. This can be accomplished for example by Inserting vibratory rods at specified locations and may even require additional concrete to be added. Furthermore, augmented reality methods can also be utilized to more easily view areas of Issues (see, e.g., U.S. Pat. Nos. 8,922,590 and 8,943,569, both Incorporated herein by reference).

After placement and consolidation, the UAV (drone) can periodically scan the topography of the concrete article using, for example, image devices, such as optical telemetry or terrestrial laser scanning to determine areas of high and low spots that require refinishing. During the screeding process and the Initial floating process (which includes bull floating, straight-edging and darbying), the UAV can periodically scan the concrete article and determine properties such as surface moisture, which can be determined through optical telemetry (for example, light reflectance, or comparing past images with the current image), through near infrared sensing, which is sensitive to water (See e.g., U.S. Pat. No. 7,265,846, incorporated herein by reference), through radar (See e.g., U.S. Pat. No. 9,207,323, incorporated herein by reference), among other methods. Periodic scanning can include continuous scanning, or can include continual scanning such as, for example, fly-bys every 5 minutes, or every 10 minutes, or however frequent is deemed necessary based on how fast the concrete is setting or a change in the rate of setting. The path of the fly-by can also be varied, based on, for example, the region of a concrete article that is being monitored, or simply unobstructed flight paths. When measurements are collected over time and spatially over the concrete article, predictive mathematical models can be constructed such that the surface moisture can be predicted. Such models can be used to send to contractor at the building site useful Information. Mobile applications or augmented reality methods can be used on lap tops or smart phone devices to indicate sections of poured concrete having, for example, surface moisture that will soon exceed a predetermined threshold, whereby the contractor can determine when and where screeding and initial floating must be completed (See block 42 of FIG. 3). Any screeding and/or initial floating outside of the applicable workability window will result in dusting or scaling of the concrete surface, and hence repair costs that should be avoided.

Figure 4:
FIG. 4 is a graphic illustration depicting a slab that is measured in two pour locations, marked by the moisture content (i.e. $M_A$ and $M_B$), at a specific time, t=20 min, in accordance with certain embodiments of the present invention.
Figure 5:
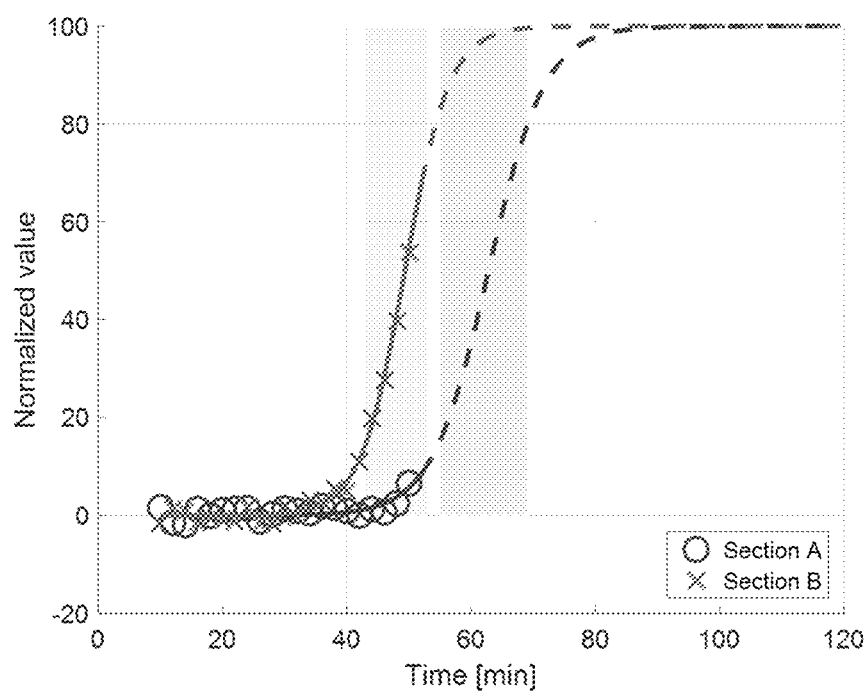
FIG. 5 is a plot of normalized moisture values that are measured for each section, A and B, over time, where the markers "O" and "X" represent measurements by an UAV, the solid line represents a fit logistics curve, the dotted line represents a future prediction, and the shaded areas note windows of optimal finishing, in accordance with certain embodiments.

FIG. 4 illustrates a bird's eye view of a poured concrete slab. This begins a discussion of how one can generate helpful mathematical models for generating visual indications of set time behavior for poured stabs. Moisture measurements are taken in two poured sections A and B (shown side by side for sake of convenience). FIG. 5 illustrates the moisture of each slab section A and B (66 and 75%) at a specific time (t=20 minutes). Measurement locations do not have to be aligned in a grid fashion, or taken consistently in the same location. For this discussion, the location of the measurements over time will be held constant. Measurements are taken in each of the two locations (at A and B shown in FIG. 4) over time. As more data is gathered, the model can be refined in real time. In other words, for each new data point that is collected, the model is rebuilt or refined to take into account the new data. The predictive models aim to detect one or more features in data curves that relate a monitored property (e.g. temperature, strength, set time or moisture) over time. A feature may be a local or global extrema (e.g. a peak or a valley), or an inflection point, or simply exceeding or falling below a pre-defined threshold. For this case, it is assumed that the inflection point of the curve representing the moisture over time represents the optimal time to finish the concrete. Again, finishing the concrete requires a minimum stiffness of the slab and a maximum moisture on the surface. Furthermore, as the concrete hardens, and more water leaves the surface, finishing becomes more difficult. Thus, optimal time exists.

In FIG. 5, the complete moisture evolution through the optimal time and beyond is plotted for each section. The markers "O" and "X" represent the data collected, while the line represents a logistic function fit using standard least-square methods. The shaded region indicates a suitable finishing window for sections A and B. This can be determined through comparisons between historical data, for example, penetration tests (see e.g. ASTM C403-16) that measure the finishing window directly and compared to sensor data signals obtained over the same time period. As can be seen, the inflection point exists within the window. Thus, if the inflection point can be determined in real time, the contractor can be alerted to start the finishing process.

In some cases, it may be more useful to alert the contractor at the start of the finishability time window, instead of in the middle of the window. In this case, the second derivative can be calculated using standard calculus techniques on an assumed form of a function that is fit to the data (e.g., a logistics function, a quadratic function, a linear function, etc.). The second derivative with respect to time can also be calculated numerically using finite differences. Using the latter process, smoothing of the original data may be necessary, although an assumed function form (e.g. logistics function) does not have to be assumed, which can be an advantage in some cases where the form of the function is difficult to determine a priori.

Figure 6:
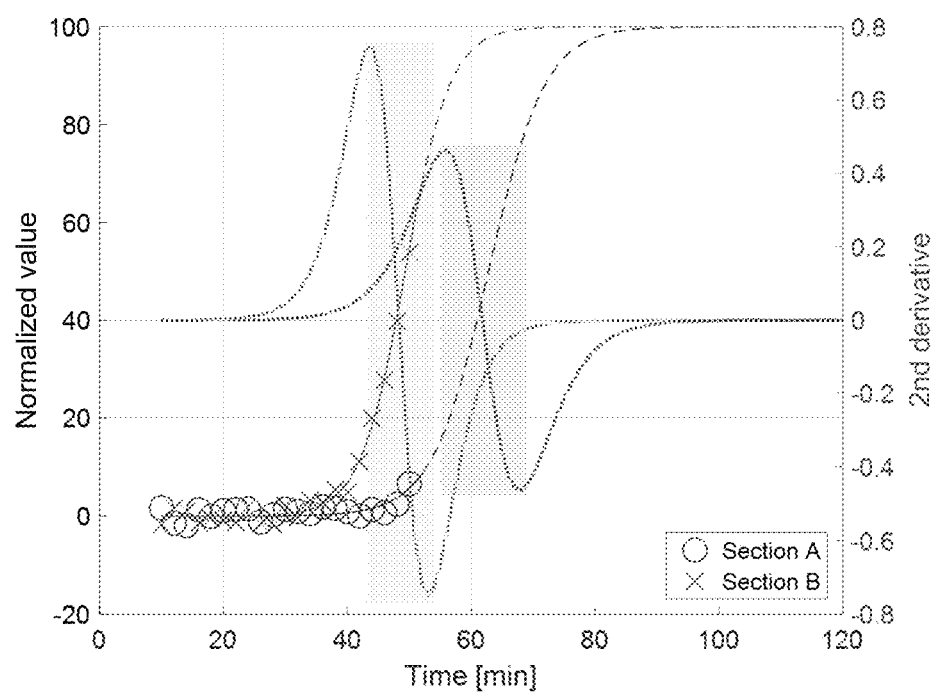
FIG. 6 is a plot of normalized moisture values including the second derivatives, which show that local extrema can be related to the windows of optimal finishing, in accordance with certain embodiments.

FIG. 6 is a graphic illustration of another exemplary embodiment wherein second derivative can be used to generate higher resolution of data to suggest when finishing can be initiated or completed.

Additionally, further analysis can be carried out to predict time values when finishing can start and end. Taking the third derivative with respect to time can help to monitor how close the third derivative is to zero, which indicates the maximum or minimum in the second derivative. Based on how fast the third derivative is converging to zero, the times at which the maximum and minimum occur (and thus the start and end of the finishing window), can be predicted and reported to the contractor or other jobsite personnel.

After initial floating operations are done, a slight stiffening must occur in the concrete before edging or jointing are performed; such stiffening is described as " . . . sustain[ing] [a] foot pressure with only approximately ¼ in. (6 mm) indentation." See e.g., ACI 302.1R-15. Alternatively, a drone-carried sensor can be used for periodic monitoring of properties such as concrete stiffness through a pressure means (e.g., a force probe or penetrometer mounted on the drone); through ultrasonic transducer/receiver/transmitter unit for measuring shear acoustic waves or Rayleigh waves; or, as another example, through electrical resistivity or temperature sensors. Continual measurement over time and space (area of the concrete article such as a slab) enables a predictive mathematical model to be constructed such that the stiffening can be predicted similar to what was described previously. For example, monitoring the temperature for initial set can indicate the time to finish the concrete article. By taking the second derivative of the temperature with respect to time (either using an assumed function or via finite differences), a local maximum in the second derivative can indicate initial set. A similar approach can be taken with outputs from other sensors as previously mentioned. This information can be presented using such mathematical models, so as to provide visual indications as to which parts of the poured concrete sections exhibit sufficient (e.g., exceeds a predefined threshold). Using this information, the contractor can direct finishers to begin power floating and troweling on specific sections of the concrete. The placed order of the concrete may not correspond to the sections requiring earlier attention, as the concrete that is placed, for example, in areas more exposed to sun or wind may have accelerated set time behaviors; or the inconsistency in the truckloads of concrete (especially concerning water content) for example (see e.g., block 44 of FIG. 3) can also change set time behavior.

Once the power floating is complete, and during the troweling operation, the UAV can periodically scan the concrete article and determine surface color and texture through optical telemetry or terrestrial laser scanning (block 46 of FIG. 3). Continual measurement over time and space (area of the article, e.g., area of a slab) enables a comparison between locations so that locations that are out of specification (e.g. via color analysis) or have not been finished (e.g. via texture analysis) can be relayed to the contractor (again, for example, through a mobile application or augmented reality method) to indicate which areas that no longer need to be troweled, and areas that still require finishing (block 50). This can prevent detrimental surface color and texture variation.

While FIGS. 4-6 illustrate the use of time and space models for a simple grid consisting of two sections where measurements were collected in the middle of the sections at regular intervals, FIGS. 7a-d demonstrate how a predictive model can be developed through use of data collected using one or more sensors onboard an unmanned aerial vehicle (UAV), commonly referred to as a drone, in a more complex, but more generalized fashion.

Figure 7A:
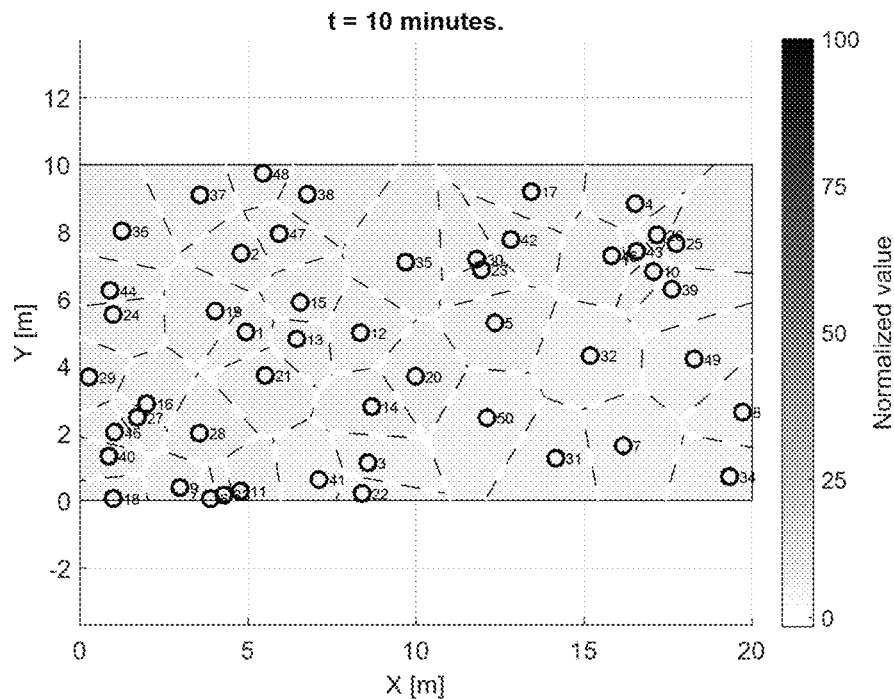
FIG. 7a is a plot of hypothetical measurements collected using a UAV (drone with sensor) at time 10 minutes after a reference time point, in accordance with certain embodiments.

In FIG. 7a, fifty hypothetical measurements have been collected by use of sensor on a drone, each measurement location noted by a circle with a number next to it. It is not necessary that the measurements are made in a regular grid fashion. In each of 7a-d, a Voronoi diagram was created using the fifty measurements. Each Voronoi "cell" is an area associated with each measurement. This is a standard method to partition an area into regions based on a group of points within the area. In essence, for each measurement, the area, or cell is defined as all areas closer to that measurement than to any other measurement. FIG. 7a employs a shade of grey for each region corresponding to a normalized value. For example, this could represent the moisture, temperature, or stiffness of the article, or even an acoustic measurement. FIG. 7a further illustrates the normalized value across the article ten minutes after a reference time (e.g. when the concrete was placed or when the concrete was batched).

Figure 7B:
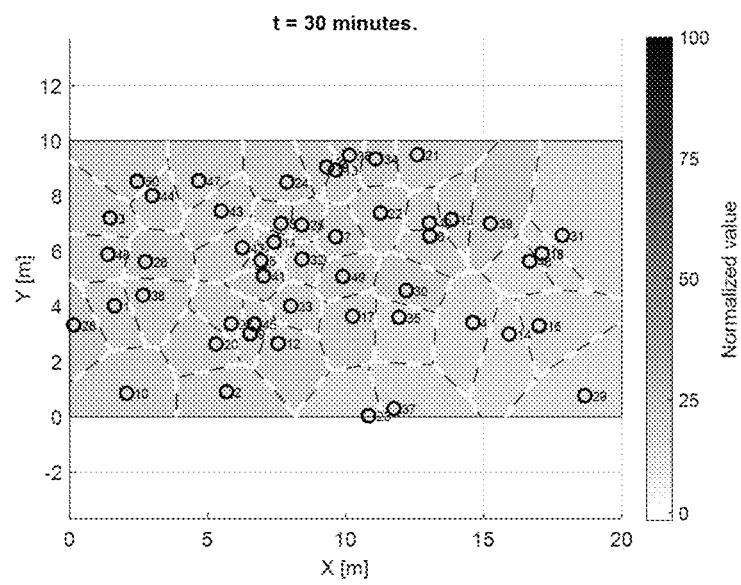
FIG. 7b is another plot of hypothetical measurements collected via a UAV at time 30 minutes after a reference time point, in accordance with certain embodiments.
Figure 7C:
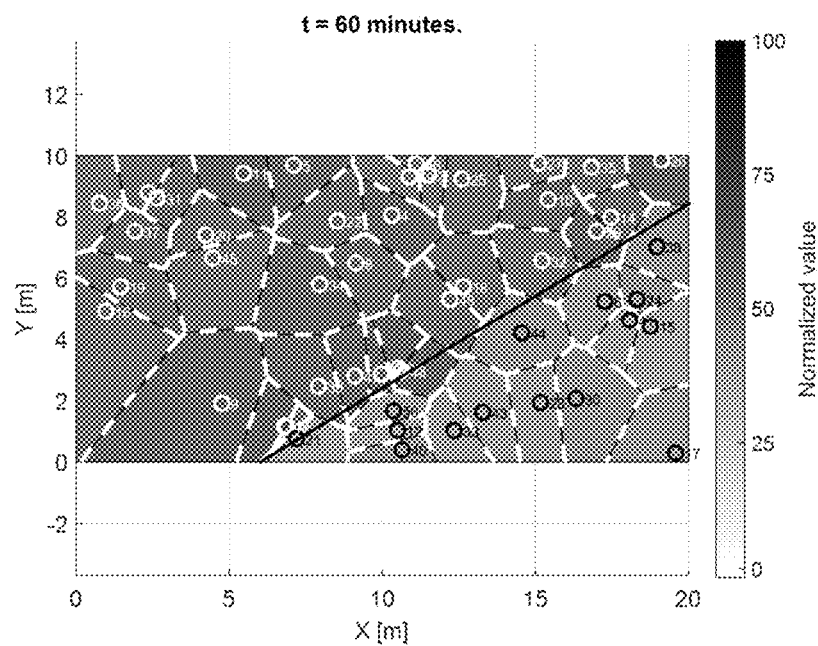
FIG. 7c is another plot of hypothetical measurements collected via a UAV at time 60 minutes after a reference time point, in accordance with certain embodiments.
Figure 7D:
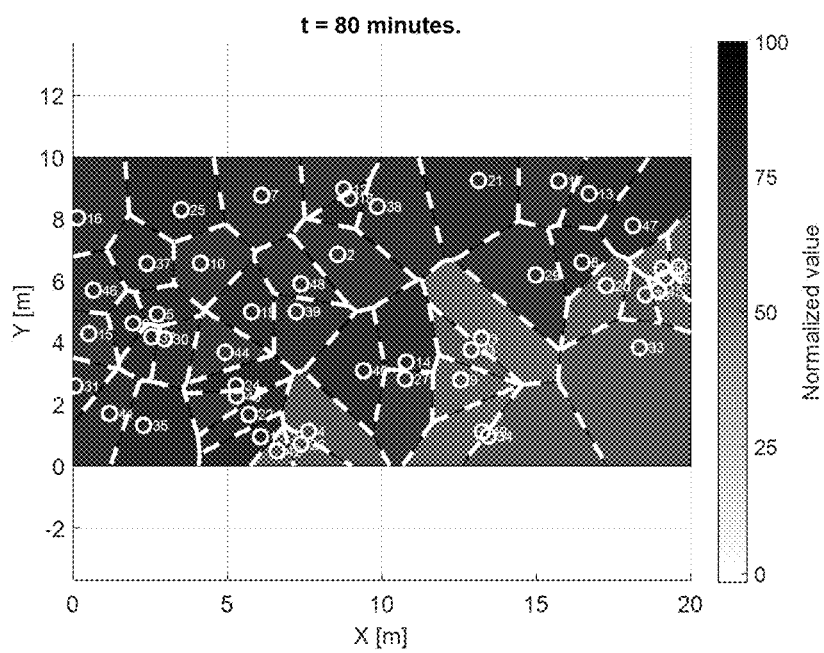
FIG. 7d is another plot of hypothetical measurements collected via a UAV at time 80 minutes after a reference time point, in accordance with certain embodiments.

FIGS. 7b-d illustrate subsequent hypothetical set time value (hydration state) measurements using one or more sensors on a drone (UAV), positioned above various sections of poured concrete, at times of 30, 60 and 80 minutes, respectively, after a reference time. The measurements do not necessarily have to be at the same locations as the previous time period. If different locations are measured over time, preferably numerous measurements should be taken to obtain a representative sampling. It is envisioned that similarly behaving regions of poured concrete can be grouped together (e.g., if a temperature difference between the two is below a pre-defined threshold). As time progresses, as shown in the exemplary embodiment illustrated in FIGS. 7a through 7d, the shaded regions become darker, but not all at the same rate. In particular, the lower right-hand corner does not become darker as fast as the rest of the article. This can simply be a result of this section being poured at a later time than the rest of the article, or a more complicated reason, such as the concrete mix is not the same (e.g. a different water content in a particular load). In any event, using the data collected at each time period for each region (in this case, the lower right-hand corner region and the complementary region), a relationship or model over time can be developed.

Figure 8:
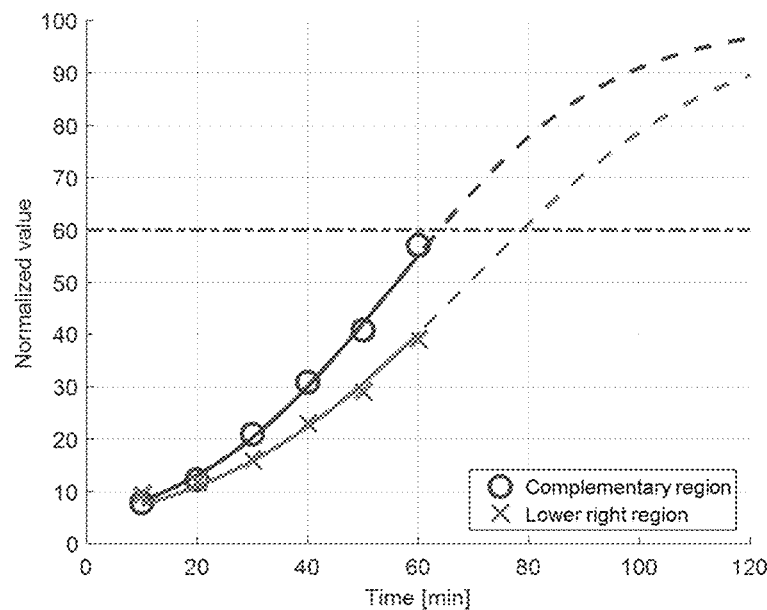
FIG. 8 is a plot of sensor data for two concrete placement regions over time, along with a predictive model fit to each set of data.

FIG. 8 illustrates a hypothetical example of the model suggested above. Each marker represents the average sensor measurement or data signal value for a particular region at a given time period. At 60 minutes, the data is used to fit a model to predict future behavior, which is represented by the dotted portion of each curve. The horizontal dash-dotted line can represent a threshold to trigger a finishing event such as "Begin power floating." This trigger point can be determined by comparing the measurements to empirical data obtained from past deliveries. More preferably, a specific characteristic (or combination of characteristics) can be correlated to the trigger point.

FIG. 8 also illustrates how a logistic function can be used for the model. The trigger point can be correlated to an inflection point on a logistic data curve, for example the point at which the curve changes from concave to convex (or vice versa). Using this example, power floating of concrete sections indicated in the lower right region of FIG. 7c can begin in about 20 minutes, while power floating for other sections can begin in approximately 3 minutes. This predictive tool can prevent serious surface damage from power floating activities that begin (for example) too early or too late.

Many different sensors can provide measurements over both time and space to yield information that can indicate when to start and complete different phases of the finishing process. Relationships can be developed between physical phenomena such as changes in surface moisture or stiffness of the concrete article. Some of these relationships exist in the literature, for example the relationship between penetration tests and slab stiffness. Other relationships require more in-depth analysis and additional parameters. For example, if using an optical sensor, machine vision (see e.g., *Machine Vision*, R. Jain, R. Kasturi, B. Schunck) can be a useful mathematical tool to pick out characteristics over subsequent images that can relate to, for example, changes in surface moisture. Determination of color, shading and texture characteristics can be particularly useful. For example, the mean intensity, entropy, energy, contrast, homogeneity and correlation calculations can be used to analyze subsequent images over time (see e.g. *Machine Vision*, R. Jain, R. Kasturi, B. Schunck, pp. 234.248). Different characteristics will be more or less sensitive to different situations (e.g. an indoor slab versus and outdoor slab).

Aside from improving finishing operations, drones have other uses. For example, the same method to collect data from the concrete article both in a temporal and spatial manner, can be used to generate a mathematical model for temperature, hydration (e.g. initial and final set), concrete strength (e.g. via a maturity method such as ASTM C1074-17), and moisture changes over time. As each point or group of points are recorded, the sensor measurement(s) can be fed into a processor such that the predictive model can be regenerated, or updated to include the new data points. Thus, the predictive model adapts to new data and is not just a static model. This prediction can further enable the contractor to make logistic decisions at the jobsite.

Furthermore, set time predictions (initial and final set as well as times to start surface finishing or times that the surface finishing can be completed by) can be recorded along with all other data associated with the concrete including what concrete delivery truck loads contributed to the section of concrete article, the batch weights for each concrete delivery truck load, the slump of each concrete delivery truck load, other rheological characteristics of the concrete delivery truck load, the air content of the concrete delivery truck loads, total water and admixture dosages including those dosed during transit for each concrete delivery truck load, etc. By collecting these data as they are generated and recording the data in a database, additional predictive models can be generated which related the associated data for a given load (i.e. pre-pour data) to post-pour data including set time. Thus, for a given concrete delivery truck load being directed to a particular job site, the set time can be predicted. This is illustrated through Example 4 described hereinafter.

Alternatively, set time estimations can be obtained by assuming a particular load for the same job has a similar set time to a previous load given that the pre-pour conditions are similar (e.g. the total water content is within 5 pounds per cubic yard of concrete, or the slumps are within 1", etc.). By using the predicted set times and comparing to a target set time, a difference in set times can be established. Based on this difference, along with any extra time required, an appropriate dosage of set retarder can be calculated and administered to adjust concrete set times, so that placement of concrete enroute or re-routed can be coordinated, as explained in the detailed explications of hypothetical illustrations which follow.

Figure 9:
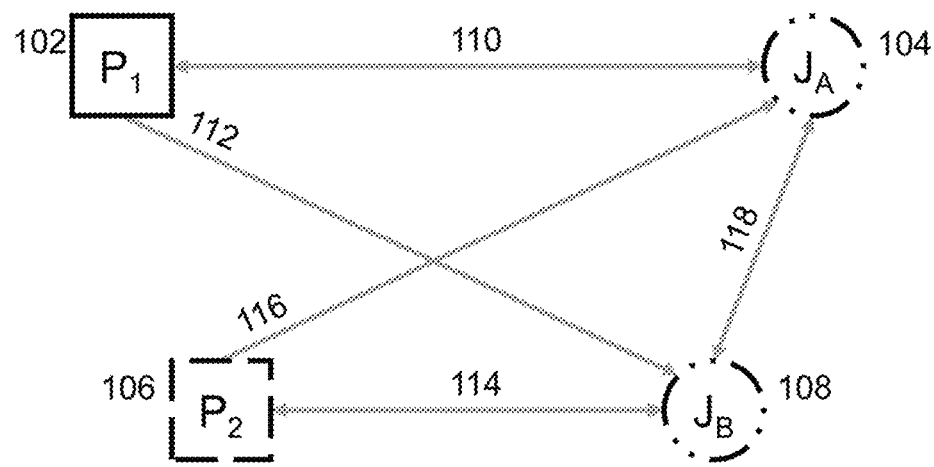
FIG. 9 is a diagrammatic illustration of concrete delivery truck routes in accordance with certain embodiments.

FIG. 9 illustrates an example of two batch plants which each normally supply two job sites. The present invention enables a partial or complete load, unused or rejected at one of the sites, to be sent directly or indirectly to the other site. The route 110 between Plant 1 ($P_1$ at 102) and Jobsite A ($J_A$ at 104) has a transport time of 45 minutes (1 way). The route 114 between Plant 1 to Jobsite B ($J_B$ at 108) has a transport time of 25 minutes. The route between Plant 2 ($P_2$ at 116) and $J_B$ has a transport time of 10 minutes. The route 116 between $P_2$ (106) and $J_A$ (104) has a transport time of 6 minutes. The route 118 between the two jobsites $J_A$ and $J_B$ has a transport time of 12 minutes.

With reference to FIG. 9, assuming for illustrative purposes that Plant 1 (102) is dedicated to delivering to Jobsite A while Plant 2 (106) is dedicated to delivering to Jobsite B (108), the present invention enables a scenario wherein concrete from Plant 1 to Jobsite A (104) is rejected at Jobsite A but can be delivered to Jobsite B (108). To receive a ticket authorizing this rerouting, or to make adjustments to the mix (e.g. add cement), the concrete delivery truck must ordinarily travel route 110 in both directions (i.e., it must return to Plant 1 at 102) and then travel route 112 to Jobsite B at 108. The total time required by this travel distance is 45×2+25=115 minutes (not counting the time for receiving the ticket and making any adjustments to the concrete). Ordinarily, Jobsite B (108) receives concrete from Plant B (106) by way of route 114 which normally requires only 10 minutes. Thus, the rejected delivery from Plant 1 is 105 minutes older (115 minus 10=105) as compared to typical deliveries from Plant 2 to Jobsite B which travel along route 114. It is not surprising, then, that the finishing time of the concrete from Plant 1 will be different compared to the concrete from Plant 2. This leads to serious issues, as the concrete from Plant A could set 105 minutes earlier as compared to the concrete ordinarily delivered from Plant B (106) to Jobsite 8 (108).

With reference to FIG. 9, assuming for illustrative purposes of another example, if we consider that concrete from Plant 2 (106) to Jobsite B (108) by route 114 is rejected for use at Jobsite B, then for purposes of re-use at Jobsite A, the delivery truck must ordinarily travel route 114 twice (since it must ordinarily return to Plant 2 to obtain a ticket authorizing delivery to Jobsite A) and then travel route 116 to Jobsite A. The total time (again, not including the time to receive a new ticket and adjust the mix design) will be 10×2+6=26 minutes. This is 19 minutes less than typical concrete deliveries from Plant 1 to Jobsite A. Concrete from Plant 2 arrives sooner to Job A and will set 19 minutes later in time as compared to concrete from Plant 1.

In a further exemplary illustration based on FIG. 9, let us assume that Plant 1 (102) is dedicated to delivering to Jobsite A (104), while Plant 2 (106) is dedicated to delivering to Jobsite B (108). Also assume that a concrete load delivered from Plant 1 to Jobsite A is rejected, but can be delivered to Jobsite B. In exemplary embodiments of the present invention, an electronic ticket can be issued as soon as the concrete delivery truck is confirmed to deliver to Jobsite B. This eliminates the need to have the concrete delivery truck, situated at Jobsite A, return to Plant 1. The delivery time from Plant 2 to Jobsite B can be sent to the processor for the concrete management system that controls the monitoring of the concrete load on the concrete delivery truck. This can be based on, for example, the time of the last delivery, an average of several past deliveries, or a forward prediction of the next delivery. The processor also receives an estimate for the current concrete delivery truck to reach Jobsite B from Jobsite A, including time the concrete has already traveled from Plant 1 to Jobsite A. In this case, the delivery time from Plant 2 to Jobsite B via route 114 is 10 minutes, and the delivery time from Plant 1 to Jobsite A and from Jobsite A to Jobsite B will be a total of 57 minutes. Thus, the concrete originating from Plant 1 will be 47 minutes older than concrete originating from Plant 2. In this case, the processor calculates the amount of retarder required to retard the concrete by 47 minutes, and the retarder is dosed on the concrete delivery truck accordingly. The dosage may be carried out manually or automatically.

FIG. 9 also allows one to consider a further scenario enabled by the present invention, where a concrete delivery from Plant 2 (106) to Jobsite 8 (108) is rejected for use at Jobsite B, but could be used at Jobsite A. In this case, once the delivery from Plant 2 to Jobsite B occurs the concrete is needed for Jobsite A, an electronic ticket can be issued (e.g., to the processor-controlled management system onboard the delivery truck), thus eliminating the need for the truck to return to Plant 2 and then to have to travel from Plant 2 to Jobsite A. The delivery time from Plant 1 to Jobsite A can be sent to or stored on the truck, as well as an estimate for the current concrete delivery truck to reach Jobsite A including time already traveled. Thus, in this example the delivery time from Plant 1 to Jobsite A is 45 minutes and the delivery time from Plant 2 to Jobsite B and from Jobsite B to Jobsite A totals 22 minutes. Thus, the concrete originating from Plant 2 will have been batched 22 minutes after the batch time for the concrete which is typically delivered to Plant 2 from Plant 1. In this case, the processor calculates the amount of accelerator needed to accelerate the concrete by 22 minutes, and the accelerator is dosed on the concrete delivery truck. The accelerator may be dosed either manually or automatically. Alternatively, the concrete delivery truck driver or jobsite coordinator is instructed to wait approximately 22 minutes before pouring the concrete.

In a still further example of the advantages and features of the present invention, using FIG. 9 as an illustration, let us assume Plant 1 (102) is dedicated to delivering to Jobsite A (104) and Plant 2 (106) is dedicated to delivering to Jobsite B (108). Assume also that a concrete delivery truck that travels from Plant 1 to Jobsite A is rejected, but it can be delivered to Jobsite B. Additionally, the mix design of the current concrete delivery truck needs to be adjusted to match the mix requirements of the concrete article at Jobsite B. An electronic ticket is issued as soon as the concrete delivery truck is confirmed to deliver to Jobsite B. A processor accessible by the concrete delivery truck receives the delivery time from Plant 2 to Jobsite B. This can be based on, for example, the time of the last delivery, an average of several past deliveries, or a forward prediction of the next delivery. The processor also receives a time estimate for the current concrete delivery truck to reach Jobsite B including time already traveled and an estimate of the time required to adjust the mix design in the concrete delivery truck, which will involve batching at a given plant. At this point, the processor is programmed to consider two alternatives. The first alternative is for the concrete delivery truck to return to Plant 1, adjust the mix and travel to Jobsite B. The second alternative is for the concrete delivery truck to travel to Plant 2, adjust the mix, and travel to Jobsite B.

For the first alternative, the total time between Plant 1, Jobsite A, back to Plant 1 and Jobsite B [via routes 110, 210 and 112] is 45×2+25=115 minutes (excluding time to adjust the mix design). The time difference between this travel time and the time estimate between Plant 2 and Jobsite B is 115−10=105 minutes. Thus, a retarder is required. Within this alternative, at Jobsite A, the concrete will be dosed (automatically or manually) with a retarder to adjust for the 105 minutes. Once the concrete delivery truck is adjusted at Plant 1, the additional materials added can be dosed with a retarder to cover the travel time between Plant 1 and Jobsite B. The entire dosage may be added at Jobsite A.

For the second alternative, the total time between Plant 1, Jobsite A, Plant 2 and Jobsite B [numbers 110, 116 and 114] is 45+6+10=61 minutes, neglecting the time to adjust the mix design. The time difference between this travel time and the time estimate between Plant 2 and Jobsite B is 61−10=51 minutes. Again, a retarder is required. In this case, however, if retarder is dosed to account for the time between Plant 1, Jobsite A and Plant 2 (including any time required to adjust the mix design), no further adjustment is required since the remaining leg of the trip is the same as deliveries made directly between Plant 2 and Jobsite B.

In the above examples, the time to adjust the mix design was not included for sake of simplifying the time difference calculations. If the mix design is to be adjusted, then those of ordinary skill in the art based on the disclosures herein will understand how to adjust the time to compensate for correct age of the concrete. For both these cases, a "dribble dose" may be used. Thus, instead of measuring the exact dosage of retarder, sufficient retarder is added to take effect for a certain period of time, e.g., 15 minutes. After this period of time expires, if more retarder is required, another dose is added, and so on. This is discussed and illustrated in Example 5.

While the embodiments disclosed herein are described herein using a limited number of embodiments, these specific embodiments are not intended to limit the scope of the invention as otherwise described and claimed herein. Modifications and variations from the described embodiments exist. More specifically, the following examples are given as a specific illustration of embodiments claimed. It should be understood that the embodiments are not limited to the specific details set forth in the examples. All parts and percentages in the examples, as well as in the remainder of the specification, are by percentage dry weight unless otherwise specified.

EXAMPLE 1

Figure 10:
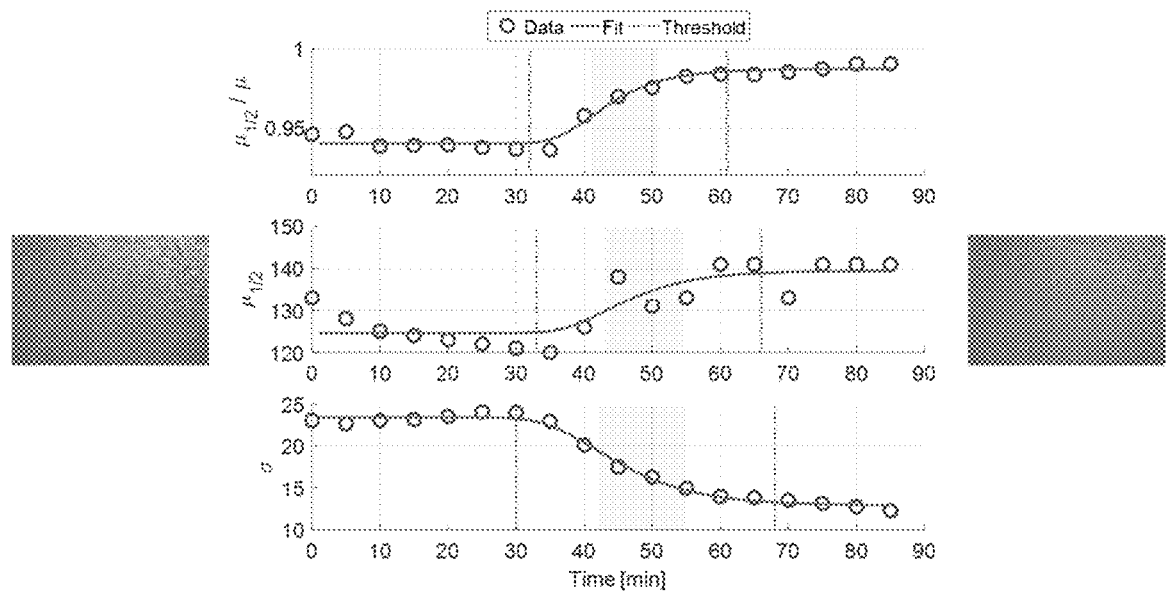
FIG. 10 is a plot of experimental results for various optical measurements of the surface of a poured concrete slab over time, in accordance with certain embodiments.

FIG. 10 graphically illustrates experimental optical measurements of a concrete slab over time. A concrete mix containing 564 pounds per cubic yard (lbs/yd$^3$) of cement, 1700 lbs/yd$^3$ of stone, 1425 lbs/yd$^3$ of sand, 300 lbs/yd$^3$ of water and 7.5 ounces per hundred pounds of cementitious materials (oz/cwt) of WRDA® 64, a low-range water reducer (LRWR). The concrete was mixed according to the following protocol: at high speed, the stone, sand, and 80% of the water was mixed for 2 minutes; cement was added with the remaining water and mixed in at high speed for 2 minutes; the LRWR was added and mixed in at high speed for 2 minutes; the mixer was turned off and the concrete was left to rest for 3 minutes; and the mixing resumed at high speed for 3 minutes. After mixing, a portion of the concrete was tested for slump and air, while the remaining concrete was poured into a 2-foot by 3-foot by 6-inch slab, screeded, and hand floated. After this, images were acquired every 5 minutes from a stationary camera (which is envisioned to be replaced by a UAV in accordance with embodiments disclosed herein). From each image, the mean, median and standard deviation of the grey level was determined using typical image analysis tools (See e.g., Solomon, C. and Breckon, T., *Fundamentals of Digital Image Processing: A Practical Approach with Examples in Matlab*, Wiley-Blackwell).

From top to bottom, the following values are plotted over 90 minutes in FIG. 10: the ratio between the median and mean, the median, the standard deviation. This data helps the formulation of a mathematical model. In this case, a generalized logistics function was fit using standard regression tools. Using these equations, the time when the water sheen disappears from the concrete surface for a given concrete section can be predicted, thus giving the contractor the ability to know when to move to the next section to finish. As previously mentioned, measurements such as this example can be made using an UAV-based sensor, and in combination with the ability to automatically collect measurements across the slab over time, can enable contractors to have greater understanding of the set time behavior of the concrete to ensure proper finishing.

EXAMPLE 2

A second concrete was prepared and mixed in the same manner as Example 1. The mix design was altered to 625 pounds per cubic yard (lbs/yd$^3$) of cement, 1700 lbs/yd$^3$ of stone, 1450 lbs/yd$^3$ of sand, 300 lbs/yd$^3$ of water and 4.5 ounces per hundred pounds of cement materials (oz/cwt) of ADVA® 190, a high-range water reducer (HRWR). A 2-foot by 2-foot by 6-inch slab was created in the same way as Example 1, and was also monitored over time by a stationary camera (again, envisioned to be replaced by a UAV-based sensor). Different from Example 1 was the location of the slab, which was put in an area where lighting was variable (e.g., cloud/sunlight changes). In FIG. 10, the median intensity for each image is shown over time. In this example, there is a poor indication of trends overtime. However, a texture analysis algorithm (See e.g., *Machine Vision*, R. Jain, R. Kasturi, B. Schunck, pp. 236-238, incorporated herein by reference) can be used to improve correlation of sensor data to set time values of the concrete.

Figure 11:
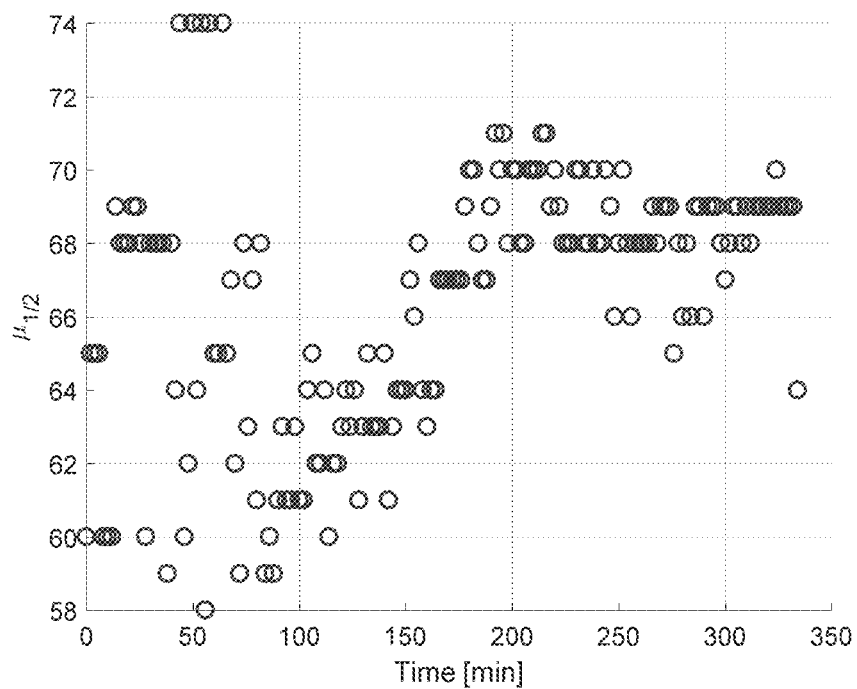
FIG. 11 is a graphic illustration of the median intensity of the color of a poured concrete segment (in terms of gray scale) overtime which can be correlated with the setting characteristics of the concrete, in accordance with certain embodiments.

As graphically illustrated in FIG. 11, the contrast analysis results are much clearer than those shown by using just median intensity. Furthermore, the minimum, which is a characteristics of the curve, can be correlated to the time for beginning the power floating process.

EXAMPLE 3

Figure 12:
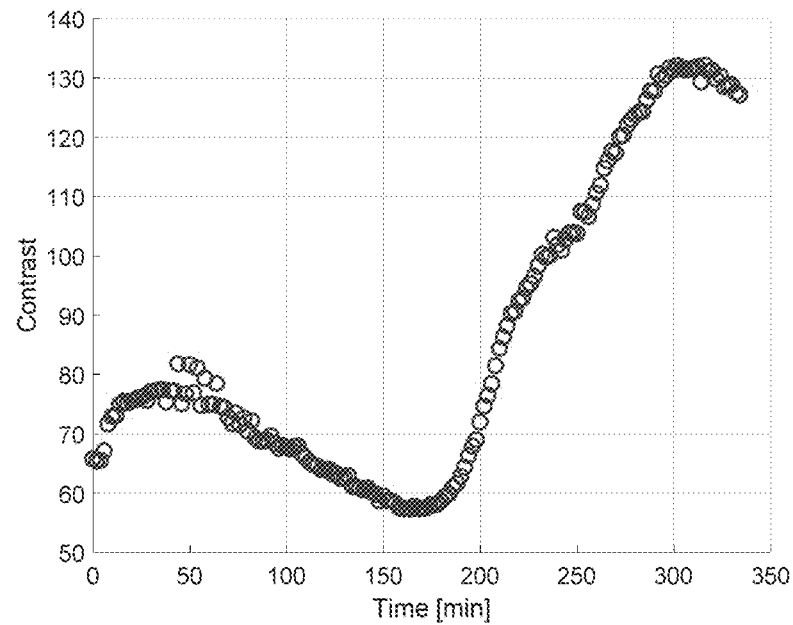
FIG. 12 is a graphic Illustration of gray-level contrast over time of a certain segment of a poured concrete slab which can be used to suggest set time value or characteristic, in accordance with certain embodiments.

The same concrete samples observed by the stationary camera in Example 2 above were observed using a near-infrared sensor, sensitive to the wave lengths in the range of 750-1000 nm. As shown in FIG. 12, after about 150 minutes, the sensor readings began to decrease in a linear fashion. This corresponds to the minimum for the contrast of the grey-level co-occurrence matrix in Example 2. Consequently, this change in behavior can be used to provide an indication or signal as to when the power floating can begin.

EXAMPLE 4

Pre-Dour Data. A system can be programmed to collect data from each concrete delivery. First, batch weights, which include the amounts of cement, aggregates, water and admixtures, are recorded and stored in a database. The batch time is also added to the database. The temperature of the materials can also be added to the database. During the delivery, any water or admixture added to the concrete delivery truck is added to the database. At the point of discharge, the final concrete temperature, the current ambient temperature, slump (or slump flow), air content (e.g. from a sensor such as commercially available under the CIDRA® brand), drum revolutions, time from batch and concrete volume are recorded. All data up to this point can be considered pre-pour data. To simulate this, 29 concrete mixes were tested in the lab. The same basic mix design was used, which includes 565 pounds per cubic yard (pcy) of an ASTM Type I cement, 1700 pcy of coarse aggregate, 1425 pcy of fine aggregate, and water that varied between 260 and 300 pcy of water. A high-range water reducer (HRWR) (e.g., ADVA*198 water reducer from GCP Applied Technologies) was used at 4.00 ounces (oz) per 100 pounds of cement (cwt), while an air entraining agent (e.g., DAREX® II AEA also from GCP) was used at 0.4 oz/cwt. All mixes were mixed using the following protocol: 1) all of the coarse and fine aggregate was placed in the mixer with 20% of the water and the air entrainer; 2) mix at a high speed for 1 minute; 3) add the cement and mix again at high speed for 2 minutes; 3) add the HRWR while continuing to mix for another 2 minutes; 4) stop the mixer and rest for 3 minutes; 5) resume mixing at a high speed for 2 minutes; 6) reduce speed and mix for another 1 minute; and finally 7) stop mixer and begin testing. Of the 48 mixes: 9 mixes did not have AEA; the curing temperature was 2° C. for 8 mixes; and the curing temperature was 38° C. for 8 mixes. For the remaining 23 mixes, the curing temperature was 20° C. Each mix was tested for pre-pour data: slump and air content.

Post-Our Data. The system also records data after the pour. To simulate this, for each mix tested for pre-pour properties, post-pour properties were also tested including Initial set time, final set time and strength at 1, 3, 7 and 28 days. The initial and final set times were estimated by analyzing the temperature evolution of 4×8 inch cylinders using typical methods (e.g. www.intrans.iastate.edu/research/documents/research . . . /CalorimeterReportPhaseIII.pdf). All data was recorded in a database.

Figure 13:
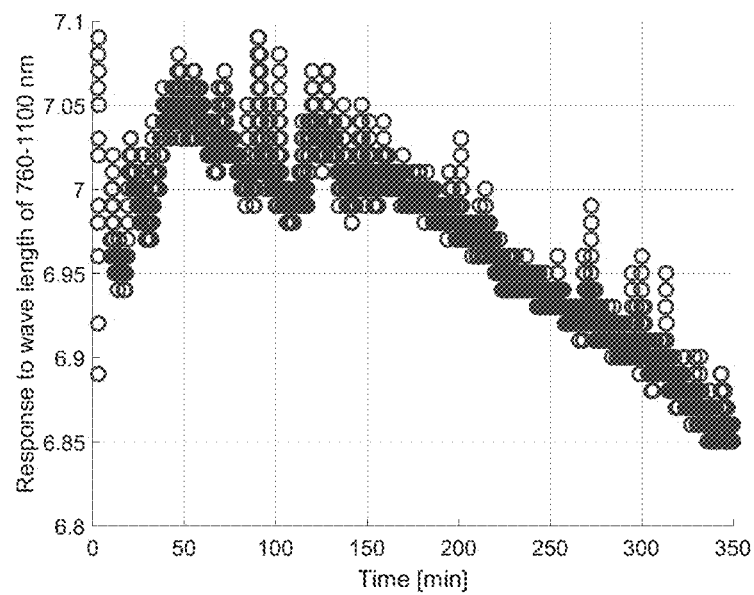
FIG. 13 is a graphic illustration of the response of an infrared (IR) sensor to wavelength of 760-1100 nm being reflected by a poured concrete segment over time, in accordance with certain embodiments.

Based on the pre and post pour data, a random forest model was developed to predict final set time was developed. The data was split into a training set (29 mixes) and a testing set (19 mixes). Both sets Included samples with different AEA contents, water contents and curing temperatures. A random forest model (e.g. see https://en.wikipedia.org/wiki/Random_forest) analysis was used to develop the model shown in FIG. 13, where the x-axis is the actual set time and the y-axis is the predicted set time. The line of equality is plotted along with the predicted points for the testing set. The model was developed using pre-pour properties: slump, air, water content, as well as the curing temperature. This curing temperature can be determined using current and near-future weather conditions at the pour site. Thus, data from a weather application can be used to calculate curing temperature.

It is noted that a variety of methods can be used to develop the model. As copies amounts of data will arise, machine learning techniques would be applicable, including supervised learning (e.g. support vector machines, Bayesian methods, random forest methods, etc.) and unsupervised learning (k-means clustering, neural networks, etc.). This will be especially suitable when considering more than one mix design. Thus, inputs for the model can be batch weights of each constituent in addition to what was used in this example.

With the developed model, set time predictions can be made based on pre-pour information from a concrete load, and these predictions can include slump, air, water content and curing temperature values or value ranges.

Predicted set time values can be compared with the set times of the concrete already placed. To coordinate the set times of concrete loads, the difference between predicted and placed set times (based on any other time required before pouring the concrete) can be set as an input to a model that calculates appropriate set retarder dosages, for example. These models take a set time adjustment as an input (e.g. 30 more minutes) and outputs a retarder dosage (e.g. 3 oz/cwt). Concrete producers typically use set retarders to adjust set time of mix designs (but usually retarders are only added at the batch plant); but nevertheless this general understanding of dosage and set time adjustment exists and is believed by the present inventors to be readily adapted for intransit/delivery pour methods of the present invention. As such, a standard model can be used for all mixes, but it is envisioned that as more data is collected (e.g. dosages administered and resulting measured set time adjustments), the models arising from implementation of the teachings of the present invention can be refined with increased amounts of data collected. Furthermore, additional inputs to the model can be used such as the mix design, batch weights, and pre-pour data (e.g. slump, air). Again, the problem lends itself to resolution through machine learning techniques.

After the set retarder dose is calculated, it can be administered into the concrete drum in order to coordinate the set times.

EXAMPLE 6

Figure 14:
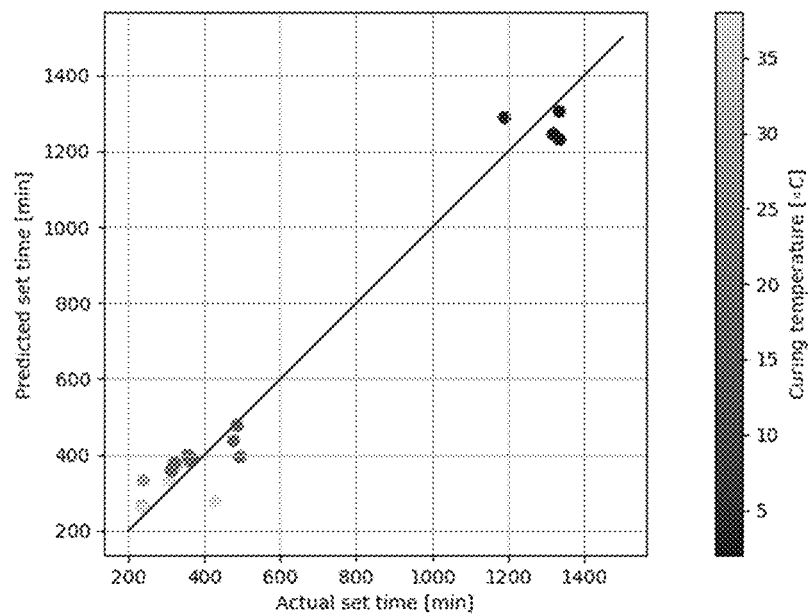
FIG. 14 is a graphic illustration of actual set time values (plotted along horizontal axis) compared to predicted set time values (plotted along vertical axis) as derived from a database of performance attributes of concrete and physical properties of the concrete such as mix design, batched weight, or water/cement ratios.
Figure 15:
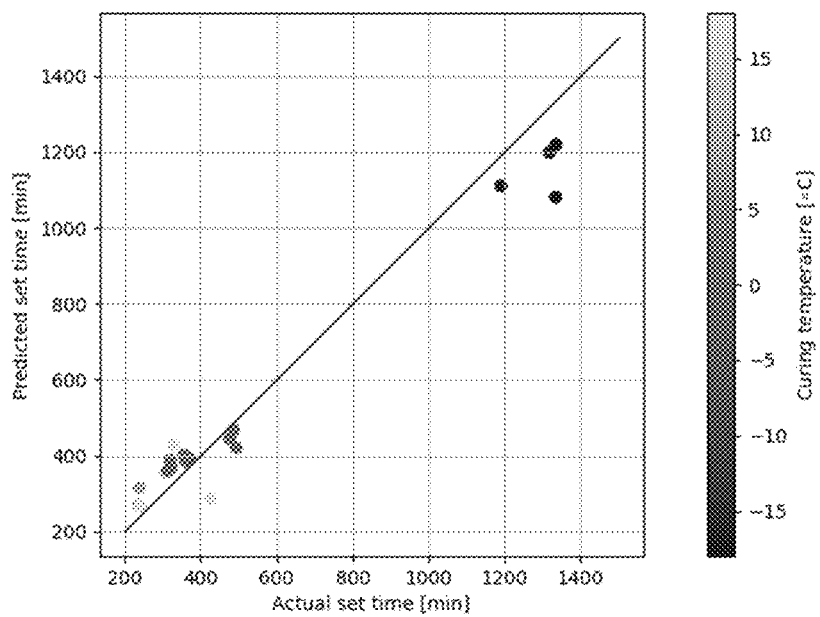
FIG. 15 is a graphic illustration of actual set time values (plotted along horizontal axis) compared to predicted set time values (plotted along vertical axis) as derived from another database of performance attributes of concrete and physical properties of the concrete such as mix design, batched weight, or water/cement ratios.

The data of Example 5 was reanalyzed using a "difference" method instead of an absolute method. That is, instead of predicting the set time based on the absolute values of temperature, slump, air, water content, a difference between a particular mix and a reference mix was analyzed. A random forest model was developed using the same method as in Example 5, and the results are shown in FIG. 14 where the x-axis is the actual set time and the y-axis is the predicted set time. The line of equality is plotted along with the predicted points for the testing set. Again, a correlation is evident, and would be improved with a larger dataset. As in Example 5, the predictive model can be used to determine a set time and thus a set time difference.

EXAMPLE 7

Same mix design of previous example. Mixing protocol: 1) all of the coarse and fine aggregate was placed in the mixer with 20% of the water and the air entrainer; 2) mix at a high speed for 1 minute; 3) add the cement and mix again at high speed for 2 minutes; 3) add the HRWR while continuing to mix for another 2 minutes; 4) stop the mixer and rest for 3 minutes; 5) resume mixing at a high speed for 2 minutes; 6) reduce speed and mix for 22 minutes to simulate travel to a Jobsite; 7) removal of 0.25 cubic feet of concrete to simulate a partial discharge; and 8) an additional 15 minutes of mixing at load speed. Three scenarios were compared: 1) no addition of Recover®, a hydration set retarder; 2) a one-time dose of Recover® immediately before mixing after the 0.25 cubic foot discharge; and 3) three or four incremental dosages (i.e. "dribbled-in"), that total the one-time dose. After mixing, the slump, air, strength and set times were measured. Set times were estimated by using a fractions method in analyzing semi-adiabatic temperature data of the concrete. The time corresponding to the temperature gain that is 21% of the maximum temperature was used for the initial set and the time corresponding to the temperature gain that is 41% of the maximum temperature was used for the final set (see e.g. http://www.nrmcaevents.ora/?nav=download&file=541).

Two different dosage levels were tested. Within each level, both the dribbled-in and one-time dose had exactly the same total dosage. The first dosage level was tested at 1.0 oz/cwt. For the dribbled-in scenarios, 4 tests were performed with an average of an 82 minute increase in initial set compared to a mix without any Recover®. The standard deviation was 24 minutes. For the one-time dose scenario, 3 tests were performed with an average of a 32 minute increase in initial set compared to a mix without any Recover®. The standard deviation was 27 minutes. It is surprising that an incremental dosage scheme provided a more consistent and larger retardation effect, as one would expect a larger, early dosage of Recover would provide the largest retardation effect.

At a 4.73 oz/cwt dose, 2 tests were performed for each scenario. For the dribbled-in scenario, the average increase in initial set time was 286 minutes, while the one-time dose scenario was 289 minutes. The standard deviations were 7 and 16 minutes respectively. Thus, at higher dosages, the difference between the two scenarios decreases. Thus, depending on the dose required, an incremental or dribbled-in scheme may be preferred.

Embodiments disclosed herein are described herein using a limited number of Illustrative embodiments not intended to limit the scope of the invention as otherwise described and claimed herein.

What is claimed is:

1. A method for monitoring set time conditions of a plurality of concrete placements each having a surface, comprising:
   moving over a plurality of concrete placement locations at a job site at least one aerial drone, said at least one aerial drone having at least one sensor for monitoring the surfaces of the plurality of concrete placements for hydration over time of the placed concrete by scanning the topography of the placed concrete to obtain data signals indicative of hydration;
   comparing the obtained data signals with previously stored data signals to obtain set time values or value ranges correlated with the hydration over time data obtained from the at least one sensor; and
   generating a pictorial diagram or map of the plurality of concrete placement locations along with set time values or value ranges, or suggested sequence priorities based on set time values or value ranges, thereby to provide indication of placements that are amenable to sequential treatment with respect to (a) initiation of finishing; (b) completion of finishing; (c) removing formwork or mold from the concrete; (d) allowing foot traffic or car traffic on the concrete; (e) releasing tensioned cables from jacks; (f) anchoring or grouting post-tensioned cables; or (g) casting further concrete on top of previously poured concrete, and when said indication indicates that placements are amenable to said sequential treatment, initiating said finishing of said placements that are amenable to said sequential treatment.

2. The method of claim 1 wherein, moving over a plurality of concrete placement locations at a job site at least one aerial drone having at least one sensor for monitoring the surfaces of the concrete placements for hydration over time of the placed concrete to obtain data signals indicative of hydration, the at least one sensor is chosen from optical, infrared, acoustic, radio wave, microwave, electrical resistivity, electrical capacitance, and ultrasonic sensors.

3. The method of claim 1 wherein, in comparing the obtained data signals with previously stored data signals to obtain set time values or value ranges correlated with the hydration over time data obtained from the at least one sensor, a pictorial diagram or map of the plurality of concrete placement locations along with set time values or value ranges, or suggested sequence priorities based on set time values or value ranges, is generated on a personal computer, lap top, or hand-held smart phone or smart watch.

4. The method of claim 1 wherein the pictorial diagram or map is generated on a hand-held device or goggles worn by a site foreperson.

5. The method of claim 1 wherein the pictorial diagram is an image of concrete delivery trucks as viewed on a pour site map.

6. The method of claim 5 wherein the pictorial image further includes digital values or colors to be overlaid upon the truck images or concrete segment images to indicate visual information regarding pour status or setting values of poured concrete segments.

7. The method of claim 1 wherein, in the step of moving over a plurality of concrete placement locations at a job site at least one aerial drone having at least one sensor for monitoring the surfaces of the concrete placements for hydration over time of the placed concrete to obtain data signals indicative of hydration, the method further comprises providing a processor that is programmed to compare the obtained sensor data with previously stored sensor data signals to obtain set time values or value ranges that are correlated with hydration of concrete over time data obtained from the at least one sensor being moved using at least one aerial drone; and further comprises providing at least five concrete delivery trucks each having a mixer drum containing a concrete load and a processor-controlled system for monitoring rheology and at least one set time value or value range of the concrete load in the mixer drum of a concrete delivery truck; and further wherein the processors are programmed to perform functions comprising: (i) accessing at least one stored set time value or value range assigned to concrete loaded in the mixer drum for delivery to a job site; (ii) calculating at least one current set time value or value range for the concrete load based on monitored hydration over time; and (iii) comparing the at least one stored set time values or value ranges with the calculated at least one current set time values or value ranges.

8. The method of claim 1 wherein, in the step of moving over a plurality of concrete placement locations at a job site at least one aerial drone having at least one sensor for monitoring the surfaces of the concrete placements for hydration over time of the placed concrete to obtain data signals indicative of hydration, the aerial drone periodically scans concrete for surface moisture at least every 10 minutes, and more preferably every 5 minutes.

9. The method of claim 1 wherein the set time value or value ranges are strength values as determined by a maturity method.

10. The method of claim 9, wherein said maturity method is ASTM C1074.

11. The method of claim 7, wherein the monitored rheology is slump, slump flow or yield stress.

12. The method of claim 7, wherein the at least one set time value or value range is initial set time, final set time, compressive strength, or a combination of these values.

* * * * *